US010670566B2

(12) United States Patent
Shih et al.

(10) Patent No.: US 10,670,566 B2
(45) Date of Patent: Jun. 2, 2020

(54) RAPID ANTIMICROBIAL SUSCEPTIBILITY TESTING USING PIEZOELECTRIC SENSOR

(71) Applicants:Wan Y. Shih, Bryn Mawr, PA (US);
Wei-Heng Shih, Bryn Mawr, PA (US);
Christopher Emery, Swedesboro, NJ (US); Xin Xu, Malden, MA (US);
Suresh Joshi, Secane, PA (US); Wei Wu, Philadelphia, PA (US)

(72) Inventors: Wan Y. Shih, Bryn Mawr, PA (US);
Wei-Heng Shih, Bryn Mawr, PA (US);
Christopher Emery, Swedesboro, NJ (US); Xin Xu, Malden, MA (US);
Suresh Joshi, Secane, PA (US); Wei Wu, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 179 days.

(21) Appl. No.: 15/777,750

(22) PCT Filed: Nov. 18, 2016

(86) PCT No.: PCT/US2016/062674
§ 371 (c)(1),
(2) Date: May 21, 2018

(87) PCT Pub. No.: WO2017/087749
PCT Pub. Date: May 26, 2017

(65) Prior Publication Data
US 2018/0335405 A1    Nov. 22, 2018

Related U.S. Application Data

(60) Provisional application No. 62/257,842, filed on Nov. 20, 2015.

(51) Int. Cl.
*C12Q 1/18* (2006.01)
*G01N 29/12* (2006.01)
(Continued)

(52) U.S. Cl.
CPC ............... *G01N 29/12* (2013.01); *C12Q 1/18* (2013.01); *G01N 29/022* (2013.01);
(Continued)

(58) Field of Classification Search
CPC ...... C12Q 1/18; C12Q 2545/10; G01N 29/12; G01N 29/022; G01N 29/036
See application file for complete search history.

(56) References Cited

U.S. PATENT DOCUMENTS 5,135,852 A    8/1992   Ebersole et al.
5,518,895 A    5/1996   Thorpe et al.
(Continued)

FOREIGN PATENT DOCUMENTS

WO    WO9101381 A1    2/1991
WO    WO9716699 A1    5/1997
(Continued)

OTHER PUBLICATIONS

International Search Report and Written Opinion; dated Mar. 7, 2017 for PCT Application No. PCT/US2016/062674.
(Continued)

*Primary Examiner* — Herbert K Roberts
(74) *Attorney, Agent, or Firm* — Mendelsohn Dunleavy, P.C.

(57) ABSTRACT

A system for and method of antimicrobial susceptibility testing includes detecting a resonance peak of a sensor provided with live microbes on a surface thereof; applying a substance to the live microbes; detecting a resonance peak of said sensor after application of said substance; determining a width of a top of each of said resonance peaks before and after application of the substance from one of: (1) a phase angle versus frequency plot where the phase angle is the phase angle of the electrical impedance of said sensor. (2) a real part of a plot of an electrical impedance versus
(Continued)

frequency of said sensor. (3) a plot of a magnitude of electrical impedance versus frequency of said sensor, and (4) a phase angle versus frequency plot where the phase angle is the phase angle between an output voltage and an input voltage of said sensor, and comparing the determined widths of tops of said resonance peaks or standard deviations of the frequency of said resonance peaks to determine antimicrobial susceptibility including the minimum inhibitory concentration (MIC).

20 Claims, 16 Drawing Sheets

(51) Int. Cl.
    *G01N 29/036*    (2006.01)
    *G01N 29/02*     (2006.01)
(52) U.S. Cl.
    CPC ....... *G01N 29/036* (2013.01); *C12Q 2545/10* (2013.01); *G01N 2291/012* (2013.01); *G01N 2291/014* (2013.01); *G01N 2291/0255* (2013.01); *G01N 2291/0256* (2013.01); *G01N 2291/02466* (2013.01); *G01N 2291/0422* (2013.01); *G01N 2291/0427* (2013.01)

(56) References Cited

U.S. PATENT DOCUMENTS

| | | | |
|---|---|---|---|
| 5,856,175 | A | 1/1999 | Thorpe et al. |
| 5,869,748 | A * | 2/1999 | Stevenson ............ G01N 29/022 324/204 |
| 6,582,929 | B2 | 6/2003 | Dunfee et al. |
| 8,460,887 | B2 | 6/2013 | Goldberg et al. |
| 8,741,663 | B2 | 6/2014 | Shih et al. |
| 8,778,446 | B2 | 7/2014 | Mutharasan et al. |
| 2012/0077206 | A1 | 3/2012 | Metzger et al. |
| 2015/0301021 | A1 | 10/2015 | Haick et al. |
| 2016/0355866 | A1 * | 12/2016 | Zeng ................. G01N 27/4166 |
| 2017/0044589 | A1 * | 2/2017 | Johnson ................. C12Q 1/18 |
| 2019/0187098 | A1 * | 6/2019 | Salvati ................. G01N 29/022 |
| 2019/0242888 | A1 * | 8/2019 | Larson ................. C12Q 1/6825 |

FOREIGN PATENT DOCUMENTS

| | | |
|---|---|---|
| WO | WO2013033049 A1 | 3/2013 |
| WO | WO2015100170 A1 | 7/2015 |
| WO | WO2015107200 A1 | 7/2015 |

OTHER PUBLICATIONS

Goswami, Manish, and Narendra Jawali. "Glutathione-mediated augmentation of β-lactam antibacterial activity against *Escherichia coli*." Journal of antimicrobial chemotherapy 60.1 (2007): 184-185.

McGovern, John-Paul, et al. "Label-free flow-enhanced specific detection of Bacillus anthracis using a piezoelectric microcantilever sensor." Analyst 133.5 (2008): 649-654.

Longo, G., et al. "Rapid detection of bacterial resistance to antibiotics using AFM cantilevers as nanomechanical sensors." Nature nanotechnology 8.7 (2013): 522.

"Antimicrobial Susceptibility Testing Using PZT Sensors," Research Report for fall, 2014-2015, 17 pages.

Shih, W., et al. "Rapid Antimicrobial Susceptibility Test," Drexel Univeristy, Coulter Translational Grant Letter of Intent, 2015, 4 pages.

* cited by examiner

RAPID ANTIMICROBIAL SUSCEPTIBILITY TESTING USING PIEZOELECTRIC SENSOR

STATEMENT OF GOVERNMENT INTEREST

This invention was made with government support under grant number 1 R41 A1 112224 awarded by the National Institutes of Health. The government has certain rights in the invention.

BACKGROUND OF THE INVENTION

1. Field of the Invention

The invention relates to methods and systems for antimicrobial susceptibility testing of microorganisms/microbes. The present invention may be particularly useful in reducing the time period required to determine drug susceptibility of microorganisms and to detect drug resistance in microorganisms, including, for example, bacterial and fungal pathogens.

2. Description of Related Technologies

Different antimicrobial agents may have different effects on different microorganisms. Some organisms, due to various resistance mechanisms, may be completely resistant to a specific antimicrobial agent while others are highly susceptible due to various resistance mechanisms. Antimicrobial susceptibility testing (AST) is used to determine whether an organism is susceptible or resistant to one or more antimicrobial agents, and usually phenotypic AST methods are used. AST plays an important role in patient care and the control of antibiotic resistance since such testing can indicate which antibiotics are most likely to cure an infection and eliminate the infecting organism before resistance can develop. Rapid AST results are critical to ensure effective antimicrobials are promptly administered to patients with severe infections, e.g. blood stream infection and sepsis. AST can also reduce the empirical prescription of broad-spectrum antibiotics that are partly responsible for the rapid increase in antibiotic resistance worldwide. AST can also be used to reduce unnecessary prescription of expensive antibiotics (such as potent broad spectrum drugs) to reduce healthcare costs, when a less expensive antibiotic can be used/substituted. Various AST methods exist to test microbes. Currently, popular and widely-used AST methods include a broth dilution test, a disk diffusion test, and an antimicrobial gradient diffusion method. In an exemplary broth dilution test for bacteria, two-fold dilutions of antibiotics (e.g. 1, 2, 4, 8, and 16 µg/ml) are prepared in a liquid growth medium dispensed in test tubes. They are then inoculated with a standardized bacterial suspension of 1-5× $10^5$ CFU/ml. Following overnight incubation at 35° C., the tubes are examined for visible growth by observation of turbidity. The lowest concentration of antibiotic that prevents growth is deemed the minimal inhibitory concentration (MIC). The miniaturization of the test by use of small, disposable, plastic 96-well trays (microbroth dilution method) has made this test practical and popular. Each tray allows approximately 12 antibiotics to be tested over a range of 8 two-fold dilutions. The cost of pre-prepared panels for this test ranges from proximately $10 to $22 each. The advantages of the microdilution procedure include the quantitative measurement of MICs and the convenience of having pre-prepared panels and the method is adaptable to test fungal organisms. The main disadvantage is the lack of flexibility of drug selections available in standard commercial panels as well as the time required to complete the test.

An exemplary disk diffusion test for bacteria is performed by applying a bacterial inoculum of approximately $1\text{-}2\times10^8$ CFU/ml to the surface of a Mueller-Hinton agar plate. Commercially-prepared, fixed concentration paper antibiotic disks are placed on the inoculated agar surface. The plates are then incubated for 16-24 hours at 35° C. The zones of growth inhibition around each of the antibiotic disks are measured. The diameter of the zone is related to the susceptibility of the bacterial inoculum and can be interpreted into categories of susceptibility (i.e. susceptible, intermediate, or resistant). The advantages of this method include its simplicity because it does not require special equipment, its flexibility for selection of disks (antibiotics) for testing and it can be adapted to test fungal organisms. This method is generally the least expensive of all susceptibility testing methods (approximately $2.5-55 per test for materials). The disadvantages of the disk diffusion test include the lack of automation of the test and inaccuracies that arise especially in testing slowly growing bacteria. The test also requires significant time to complete.

The antimicrobial gradient diffusion method creates an antimicrobial concentration gradient on a plastic strip or other substrate placed on an agar medium to determine the susceptibility. The Etest™ (bioMerieux AB BIODISK) is a commercially available version of this test. It includes thin plastic test strips with an antibiotic concentration gradient on the underside and a concentration scale marked on the upper surface. The microbial suspension is inoculated on the agar plate and the test strips are placed on the surface, similar to the disk diffusion test. After overnight incubation, the MIC is determined by the intersection of the lower part of the elliptical growth inhibition area with the test strip. Etest™ strips cost approximately $2-$3 each. As a result, this method is best suited to situations in which a MIC for only 1 or 2 drugs is needed, and again, has the disadvantage of requiring at least overnight incubation.

There are automated instrument systems available for AST. These systems can usually provide test results in a shorter period than the above-described tests because their sensitive detection systems allow detection of subtle changes in growth of microbes in the presence of antimicrobials. The MicroScan WalkAway™ (Siemens Healthcare Diagnostics) is a large self-contained incubator/reader device that can incubate and analyze 40-96 microdilution trays. It incubates the trays for the appropriate time period and then examines them periodically with either a photometer or fluorometer to determine microbial growth development, for example. It can give the results in 3.5-18 hours. The Vitek 2 System™ (bioMerieux) is highly automated and uses very compact plastic reagent cards that contain microliters of antibiotics and test media in a 64-well format. It employs turbidimetry to monitor the microbial growth during incubation. The instrument can accommodate 30-240 simultaneous tests and generate results in 4-12 hours, and the system can also perform yeast susceptibility testing.

Compared to conventional methods, automated instrument systems require less labor and can sometimes provide test results in a shorter time period. However, incubation is still required for these systems and the testing time depends to a large extent on the incubation time required for microbial growth. In order to further reduce the testing time, an antimicrobial susceptibility testing method is needed that does not require incubation of the microorganism in the presence and absence of antimicrobials.

Methods of cultivating microbes for AST tests, and testing samples of microbes within arrays with various antibiotics at various concentrations, are known in the art from, for example, U.S. Pat. No. 6,582,929. When piezoelectric sensors are used in the prior art for AST testing, they can be used to detect the by-products or environmental effects of the microbes, such as by measuring pressure changes caused by metabolic activity of the microbes as in U.S. Pat. No. 5,856,175. Piezoelectric sensors have also been used to detect the weight of microbes, although this method cannot detect if the microbes are alive, as in EP 0 215 669 A1. Piezoelectric sensors can also detect the presence of microbes within a sample solution by allowing the microbes to bind to the sensor and measuring the resonance change as the mass of the sensor changes, as disclosed in, for example, U.S. Pat. No. 8,778,446 and "Label-free flow-enhanced specific detection of *Bacillus anthracis* using a piezoelectric microcantilevers sensor," *Analyst*, 2008 May, 133(5), pp. 649-654. Piezoelectric sensors with enhanced detection sensitivity are described in U.S. Pat. No. 8,741,663, the disclosure of which is hereby incorporated by reference herein.

There remains a need for methods and apparatus that enable rapid detection of the presence of microbes in a reliable manner. This and other needs are the subject of the present invention.

SUMMARY OF THE INVENTION

In a first aspect, the present invention relates to a method of antimicrobial susceptibility testing including steps of:

detecting a resonance peak of a sensor with live microbes on a surface portion of the sensor, contacting the live microbes on the surface portion of the sensor with a substance;

detecting a resonance peak of said sensor after application of said substance;

determining either a width of a top of said resonance peaks or a standard deviation of the frequency of said resonance peaks, and comparing the determined widths or standard deviations to determine antimicrobial susceptibility, and optionally determining the minimum inhibitory concentration (MIC).

The width of the resonance peak may be determined from any one of: (1) a phase angle versus frequency plot where the phase angle is the phase angle of the electrical impedance of the sensor, (2) a real part of a plot of electrical impedance versus frequency of the sensor, (3) a plot of the magnitude of the electrical impedance versus frequency of the sensor, (4) a phase angle versus frequency plot where the phase angle is the phase angle between the output voltage and the input voltage of the sensor.

The top of a resonance peak comprises the portion of the resonance peak that is within a vertical distance of a highest point of said resonance peak that is larger than a standard deviation of phase angles of the electrical impedance, or the real port of the electrical impedance, or the magnitude of the electrical impedance, or the phase angle between the output voltage and the input voltage of said detected resonance peaks and less than about one thousand times the standard deviation. Alternatively, the top of the resonance peak can be defined as the portion of the resonance peak that is within a distance from the highest point of the said resonance peak larger than 0.01% of the total height of the said resonance peak and smaller than 10% of the total height of the said resonance peak.

In a second aspect, the present invention relates to a system for rapid antimicrobial susceptibility testing comprising:

a plurality of sensors having at least one outer surface portion, an apparatus for detecting a resonance of the plurality of sensors at a plurality of frequencies; and a processing system configured to:

determine a width of a top of first and second detected resonance peaks of at least one said sensor from one of: (1) a phase angle versus frequency plot where the phase angle is the phase angle of the electrical impedance of the sensor, (2) a real part of a plot of electrical impedance versus frequency of the sensor. (3) a plot of a magnitude of electrical impedance versus frequency of the sensor, and (4) a phase angle versus frequency plot where the phase angle is the phase angle between an output voltage and an input voltage of the sensor, and compare the determined widths or standard deviations to determine antimicrobial susceptibility.

In another aspect the system and method may employ software that executes algorithms to determine and report the MIC and an antimicrobial interpretive category, e.g. sensitive (S), intermediate (I) or resistant (R), based on guidelines from, for example, the United States Food and Drug Administration (FDA), the Clinical Laboratories Standard Institute (CLSI), the European Committee on Antimicrobial Susceptibility Testing (EUCAST), or any other organization. Software may also be used to access databases and use expert rules to compare microbial identification, microbial phenotypic biochemical information, known microbial resistance mechanisms, known microbial MIC distributions, and previously defined microbial wild type and resistant phenotypic information to modify or accept the obtained MIC value and/or antimicrobial interpretive category of the test microbe.

DETAILED DESCRIPTION OF THE PREFERRED EMBODIMENTS

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

It must be noted that as used herein and in the appended claims, the singular forms "a", "an", and "the" include plural references unless the context clearly dictates otherwise. Thus, for example, reference to "a sensor" includes a plurality of sensors and equivalents thereof known to those skilled in the an, and so forth. As well, the terms "a" (or "an"), "one or more" and "at least one" can be used interchangeably herein. It is also to be noted that the terms "comprising", "including", and "having" can be used interchangeably.

Figure 4:
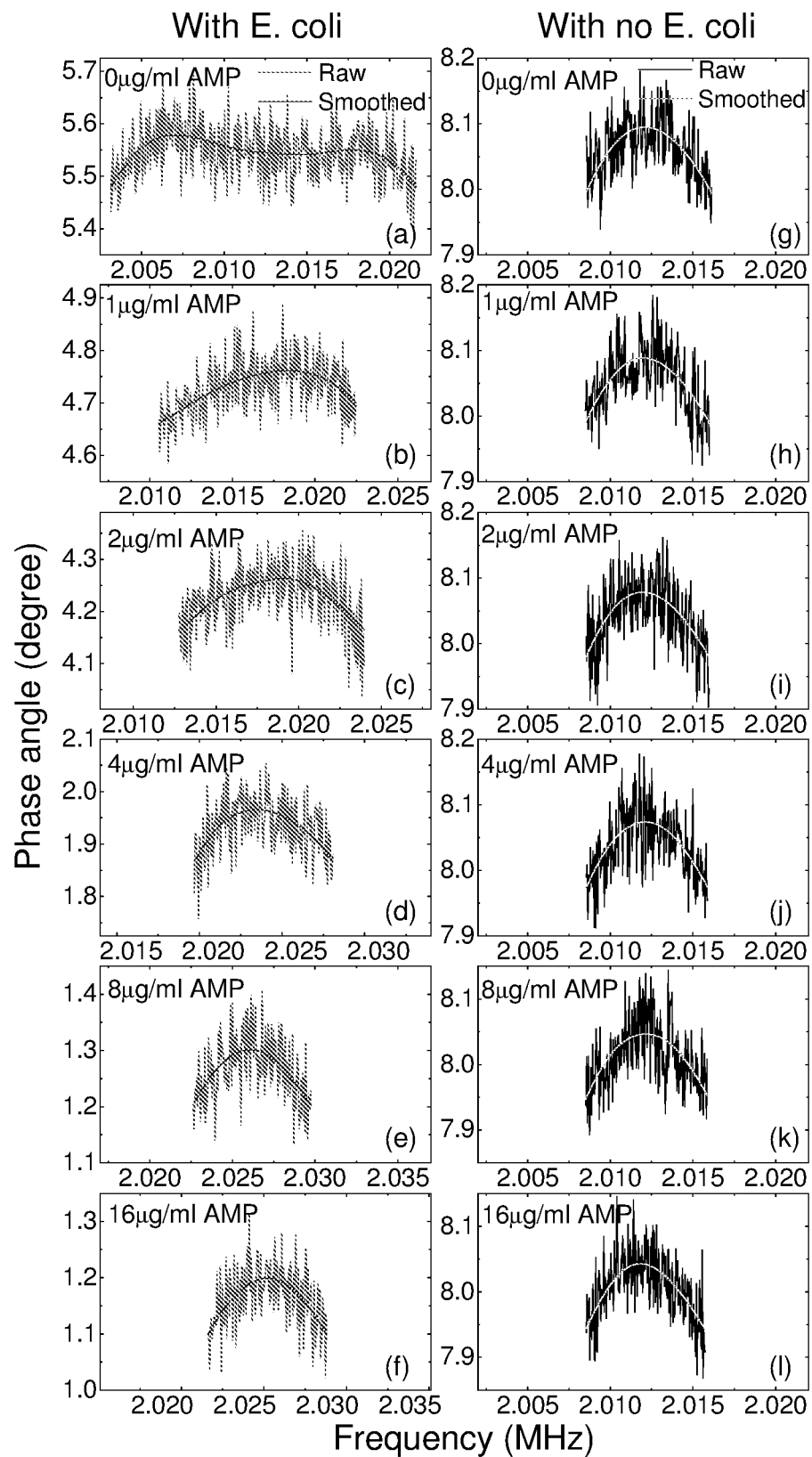
FIG. 4 shows that as bacteria on the sensor are killed with an antibiotic, in this case ampicillin (AMP), stresses produced by the live bacteria cease and the shape of the resonance peak in the phase angle versus frequency plot more closely resembles the sharper peaks of the control sensor without bacteria.

The detection sensitivity of certain piezoelectric sensors is such that they may measure minute stresses produced by live microbes which have been bound to the surface of the sensor. Live microbes generate random stresses through metabolic functions. In turn, these random stresses function to blunt the peaks of frequency resonance intensities. As shown by FIG. 4, as microbes on the sensor are killed with an antibiotic, in this case ampicillin (AMP), stresses produced by the live microbes cease and the shape of the resonance peak more closely resemble the sharper peaks of the control sensor without live microbes.

Figure 5:
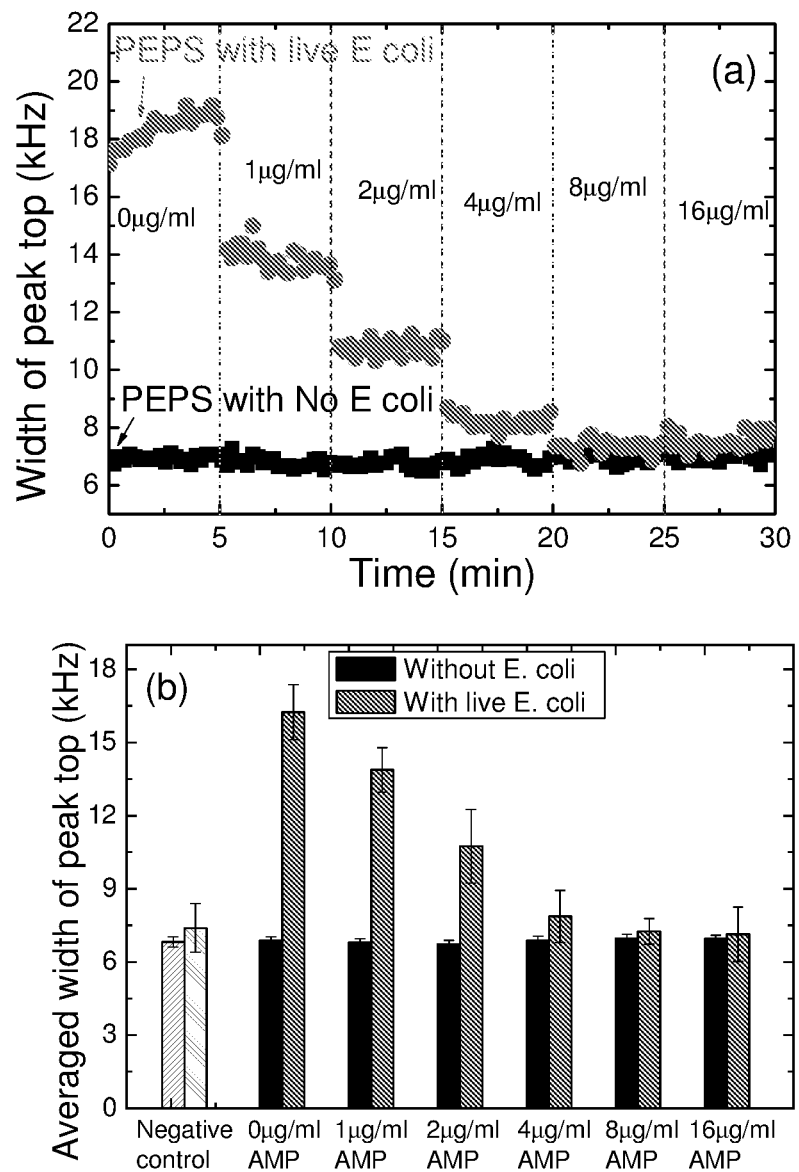
FIG. 5 shows the relationship of the width of the top of the peak plotted against rising quantities of AMP applied to the PEPS.

This relationship is even more pronounced as the width of the top of the peak is plotted against rising quantities of AMP applied to the PEPS as shown by FIG. 5. Each of the PEPS employed in the experiment to generate FIG. 5 had various concentrations of AMP, and the width of the top of the peak versus time for each PEPS was plotted for five minutes, sequentially, for a total time of thirty minutes. The 2 μg/ml AMP PEPS was exposed to AMP starting at the 10 minute mark, and was measured until the 15 minute mark. For the purpose of the tests plotted in FIG. 5, the width of the top of the resonance peak was defined as the width of the peak at a height 0.1 degree below the peak maximum.

The data plotted in FIG. 5 confirms the ability of the present method to sense and determine the minimal inhibitory concentration (MIC) of a microbe, because the known MIC of the *E. coli* that was tested is 8 μg/ml for ampicillin (AMP) [M. Goswami and N. Jawali, "Glutathione-mediated augmentation of beta-lactam antibacterial activity against *Escherichia coli*," J Antimicrob Chemother, vol. 60, pp. 184-5, July 2007].

Thus, in one embodiment, the width and/or shape of the top of a resonance peak can signify and determine the presence of live microbes. The sensor can be operated in width extension mode, which is a type of linearextensional resonance mode, but it may also be operated in other resonance modes such as a length extension mode, a thickness extension mode, a flexural mode, a width shear mode, a length shear mode, a thickness shear mode or any other suitable resonance mode which is known to the art. Width mode enables more sensitive detection with high peak frequency intensities and minimized damping effects.

Thus, the invention also includes a method of antimicrobial susceptibility testing including steps of:

detecting a resonance peak of a sensor with live microbes on a surface portion of the sensor;

contacting the live microbes on the surface portion of the sensor with a substance;

detecting a resonance peak of said sensor after application of said substance;

determining either a width of a top of said resonance peaks or a standard deviation of the frequency of said resonance peaks, and comparing the determined widths or standard deviations to determine antimicrobial susceptibility, and optionally including the minimum inhibitory concentration (MIC).

The width of the resonance peak may be determined from any one of: (1) a phase angle versus frequency plot where the phase angle is the phase angle of the electrical impedance of the sensor, (2) a real part of an electrical impedance versus frequency plot of the sensor, (3) a plot of the magnitude of the electrical impedance versus frequency of the sensor, (4) a phase angle versus frequency plot where the phase angle is the phase angle between the output voltage and the input voltage of the sensor.

The top of a resonance peak comprises the portion of the resonance peak that is within a vertical distance of a highest point of said resonance peak that is larger than a standard deviation of phase angles of the electrical impedance, or the real port of the electrical impedance, or the magnitude of the electrical impedance, or the phase angle between the output voltage and the input voltage of said detected resonance peaks and less than about one thousand times of the standard deviation. Alternatively, the top of the resonance peak can be defined as the portion of the resonance peak that is within a distance from the highest point of the said resonance peak larger than 0.01% of the total height of the said resonance peak and smaller than 10% of the total height of the said resonance peak.

Figure 6:
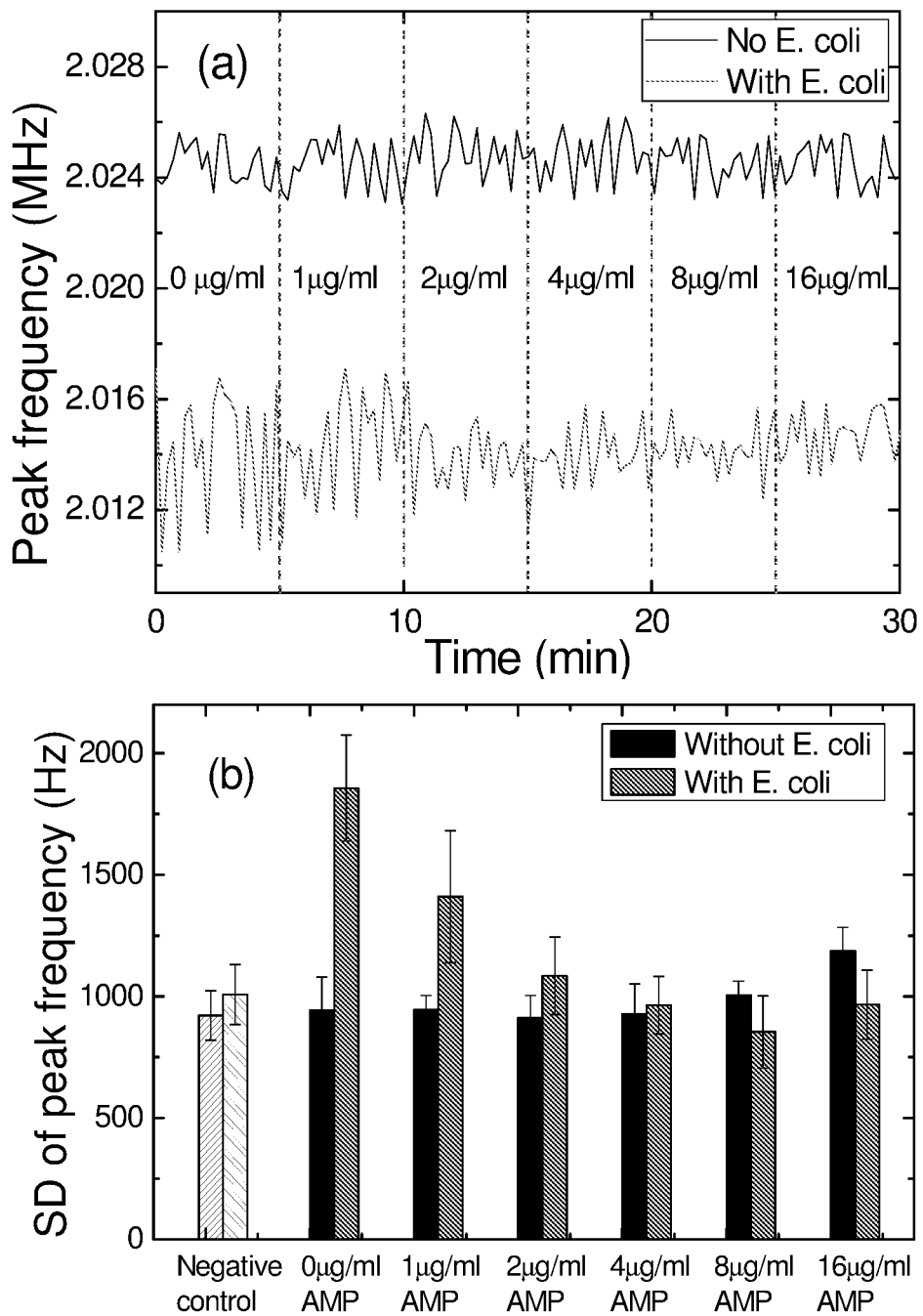
FIG. 6 shows that the noise of the peak frequency of a PEPS increases when it is coated with live bacteria, but that the noise level is reduced with increasing AMP concentrations.

Broadening of the top of the resonance peak can also lead to an increased noise level for the resonance peak frequency determination. Thus, as an alternative to determining the width of the top of the resonance peak, one can measure the noise or standard deviation (SD) of the peak frequency as an effective antimicrobial test. FIG. 6 shows that the noise at the peak frequency of a PEPS increases when it is coated with live bacteria, but that the noise level is reduced with increasing AMP concentrations. Thus, in another aspect, the present invention employs a determination and comparison of the standard deviation of the frequency of said resonance peak before and after the application of said substance instead of comparing the widths of the resonance peaks as discussed above.

The peak frequency can be either the frequency with the raw maximum phase angle or the frequency of the fitted maximum phase angle. Even though the top of a peak may be flattened the raw data can still be fitted to a peak form. Either way, the peak frequency is monitored over a period of time such as 1-10 minutes, or about 5 minutes. Upon completion of the time period, the standard deviation of the peak frequency is determined from the collected data. If the top of the peak is flattened, the standard deviation of the peak frequency will be significantly larger than if the top of the peak is not flattened, due to the uncertainty of the peak position created by the flattening of the peak. However, in practice this is not a problem since peak fitting involves portions of the peak that do not change and thus uncertainty was reduced to within acceptable limits by this factor.

In a second aspect, the present invention relates to a system for rapid antimicrobial susceptibility testing comprising:

a plurality of sensors having at least one outer surface portion, an apparatus for detecting a resonance of the plurality of sensors at a plurality of frequencies; and a processing system configured to:

determine a width of a top of detected resonance peaks of at least one said sensor from one of: (1) a phase angle versus frequency plot where the phase angle is the phase angle of the electrical impedance of the sensor, (2) a real part of an electrical impedance versus frequency plot of the sensor, (3) a plot of a magnitude of electrical impedance versus frequency of the sensor, and (4) a phase angle versus frequency plot where the phase angle is the phase angle between an output voltage and an input voltage of the sensor, and compare the determined widths of the tops of the detected resonance peaks or standard deviations of the frequency of the detected resonance peaks to determine antimicrobial susceptibility.

Sensors useful for the present invention can be a piezoelectric plate sensor (PEPS), a piezoelectric microcantilever sensor (PEMS), a quartz crystal microbalance (QCM), a surface acoustic wave (SAW) device, or any other device consisting of a piezoelectric or piezoresistive material that would allow measurement of the resonance peak using electrical means are useful for detecting the presence and/or mass of various compounds and molecules.

Sensors may be fabricated by bonding a layer of a piezoelectric material, such as commercial lead zirconate titanate (PZT), to a non-piezoelectric substrate, such as stainless steel, titanium or glass, and have a number of advantageous properties, such as the capability of electrical self-excitation and self-sensing. Furthermore, piezoelectric sensors that include an insulation layer are capable of preventing conduction in liquid media, rendering them promising for biological in-situ electrical detection.

The detection sensitivity of piezoelectric cantilever sensors, which may be viewed as harmonic oscillators, is correlated to the resonance frequency shift capability of the sensor. The resonance frequency shift capability in turn is dependent upon the ability to detect changes in the effective spring constant and effective mass of the sensor. Current cantilever sensor technologies, such as non-piezoelectric microcantilevers and piezoresistive microcantilevers are only useful for methods which detect changes in mass of the sensor. As such, they are not effective for the detection of the presence of living microbes.

Figure 1A:
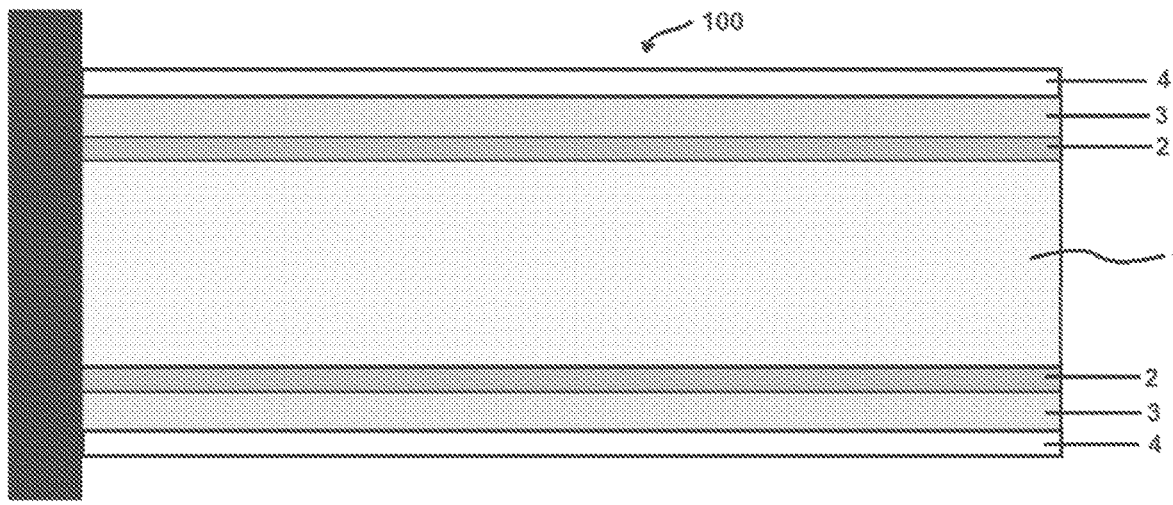
FIG. 1A shows a piezoelectric plate sensor (PEPS) that can be used in the methods of the present invention.

FIG. 1A shows an exemplary structure of a type of piezoelectric sensor, a piezoelectric plate sensor (PEPS), which may be used in the present invention. In one aspect, as shown in FIG. 1, the present invention provides a piezoelectric plate sensor (PEPS) 100, comprising a piezoelectric layer 1, two electrodes 2 positioned one on each side of the piezoelectric layer 1, an insulation layer 3 encompassing the piezoelectric layer 1 and two electrodes 2, and a binding/receptor layer 4 bound to the surface of the insulation layer 3 of the PEPS 100 for binding a biomolecule or a microbe of interest.

Piezoelectric layer 1 is positioned between electrodes 2, functioning to enable electrical detection and actuation within the PEPS 100. Piezoelectric layer 1 may function as a driving element, vibrating element, sensing element, or a combination thereof. Applying an alternating current (AC) voltage across piezoelectric layer 1 as an input induces bending and vibration of piezoelectric layer 1, which in turn induces a change in an output voltage that provides readily detectable changes in the magnitude and phase of the output voltage as well as the magnitude, phase, and real part of the electrical impedance of the sensor. The resonance frequency of the PEPS 100 may be obtained, for example, by monitoring the maximum of the phase shift of the output voltage relative to the input voltage or the phase of the electrical impedance of the sensor. This measurement may be accomplished all-electrically, i.e. using both electrical actuation and electrical sensing.

Piezoelectric layer 1 may be fabricated from any piezoelectric material, such as $(Na_{0.5}K_{0.5})_{0.945}Li_{0.055}Nb_{0.96}Sb_{0.04}O_3$ (hereinafter "Sb-NKNLN"), Sb—$(Na_{0.5}K_{0.5})NbO_3$—$LiTaO_3$ (hereinafter "Sb-NKNLT"), Sr—$(Na_{0.5}K_{0.5})NbO_3$—$LiTaO_3$ (Sr-NKNLN), Sr—$Na_{0.5}K_{0.5})NbO_3$—$LiTaO_3$ (Sr-NKNLT), SbSr—$(Na_{0.5}K_{0.5})NbO_3$—$LiTaO_3$ (SrSb—NKNLN), SrSb—$Na_{0.5}K_{0.5})NbO_3$—$LiTaO_3$ (SbSr—NKNLT), solid solutions with $(Bi_{0.5}K_{0.5})TiO_3$, $(Bi_{0.5}Na_{0.5})TiO_3$, $Ba(Zr_xTi_{1-x})O_3$, $BaTiO_3$ (hereinafter "BT"), $(Bi_{1/2}K_{1/2})TiO_3$ (hereinafter "BKT"), $(Bi_{1/2}Na_{1/2})TiO_3$ (hereinafter "BNT"), $Ba(Zr_xTi_{1-x})$ O$_3$ (hereinafter "BZT"), Bi(Zn$_{1/2}$Ti$_{1/2}$)O$_3$ (hereinafter "BiZT"), (Na$_x$K$_{1-x}$)NbO$_3$ (hereinafter "NKN"), BiScO$_3$—PbTiO$_3$ BaTiO$_3$—(Bi$_{1/2}$K$_{1/2}$)TiO$_3$ (hereinafter "BKBT"), (B$_{1/2}$Na$_{1/2}$)TiO$_3$—(Bi$_{1/2}$K$_{1/2}$)TiO$_3$ (hereinafter "BNKT"), (Bi$_{1/2}$ Na$_{1/2}$)TiO$_3$—BaTiO$_3$ (hereinafter "BNBT"), (Bi$_{1/2}$ Na$_{1/2}$)TiO$_3$—Ba(Zr$_x$Ti$_{1-x}$)O$_3$ (hereinafter "BNBZT") and (Bi$_{1/2}$ Na$_{1/2}$)TiO$_3$—BaTiO$_3$—(Bi$_{1/2}$K$_{1/2}$)TiO$_3$ (hereinafter "BNBK").

In some embodiments, the piezoelectric layer 1 is fabricated from highly piezoelectric lead magnesium niobate-lead titanate films (hereinafter "PMN-PT"), such as (Pb(Mg$_{1/3}$Nb$_{2/3}$)O$_3$)$_{1-x}$—(PbTiO$_3$)$_x$ (PMN$_{1-x}$-PTx) films, where 0.3<x<0.4, or (Pb(Mg$_{1/3}$Nb$_{2/3}$)O$_3$)$_{0.65}$—(PbTiO$_3$)$_{0.35}$ (PMN$_{0.65}$—PT$_{0.35}$); sodium potassium niobate-lithium niobate solid solutions (NKN-LN); highly piezoelectric lead zirconate titanate (PZT) films; or high piezoelectric lead-free films.

In an exemplary embodiment, piezoelectric layer 1 may be fabricated from any highly piezoelectric material with a high $-d_{31}$ coefficient in the range of from about 20 pm/V to about 5000 pm/V, or from about 200 pm/V to about 5000 pm/V, or from about 500 pm/V to about 5000 pm/V, or from about 2000 pm/V to about 5000 pm/V. In another exemplary embodiment, the $-d_{31}$ coefficient may be greater than about 20 p m/V. Additionally, piezoelectric layer 1 may have a piezoelectric coefficient $d_{33}$ greater than about 40 pm/V.

In one embodiment, piezoelectric layer 1 is made from highly piezoelectric lead magnesium niobate-lead titanate films, e.g. (Pb(Mg$_{173}$Nb$_{273}$)O$_3$)$_{0.65}$—(PbTiO$_3$)$_{0.35}$ (PMN$_{0.65}$—PT$_{0.35}$) (PMN-PT), highly piezoelectric lead zirconate titanate (PZT) films or high piezoelectric lead-free films.

Piezoelectric layer 1 may be in any form. In one embodiment, piezoelectric layer 1 is fabricated from a free standing film for enhancing domain wall motion and piezoelectric performance. When the piezoelectric material is PMN-PT, piezoelectric layer 1 may be fabricated using a precursor-suspension method. Submicron crystalline PMN powder is first prepared by dispersing Mg(OH)$_2$— coated Nb$_2$O$_5$ particles in a lead acetate/ethylene glycol solution followed by calcination at about 800° C. The crystalline PMN powder is subsequently suspended in a lead titanate (PT) precursor solution containing lead acetate and titanium isopropoxide in ethylene glycol to form a PMN-PT precursor powder, which can be sintered at a temperature as low as about 900° C.

Piezoelectric layer 1 may have any structural configuration or dimensions. Thus, piezoelectric layer 1 may be rectangular, triangular, circular, elliptical, or any other geometric shape. Piezoelectric layer 1 may have a thickness of from about 0.5 µm to about 127 µm, or from about 0.5 µm to about 100 µm, or from about 0.5 µm to about 70 µm, or from about 0.5 µm to about 50 µm, or from about 1 µm to about 30 µm. Piezoelectric layer 1 may have a length of from about 1 µm to about 5 mm and a width of from about 1 µm to about 5 mm. Piezoelectric layer 1 may have a length of from about 10 µm to about 5 mm and a width of from about 0.5 µm to about 5 mm.

Electrodes 2 of the PEPS 100 may be manufactured from a material capable of conducting an electrical signal from the piezoelectric layer 1 to a device for detecting that signal. In some embodiments, electrodes 2 are constructed from a conductive material selected from Ag, Au, Cu, Pt, Ir, Al, Fe, Cr, Ni, C, In, C, Sn, Ti and an alloy of these metals. In one embodiment, one electrode 2 is constructed from Au/Cr or P/Ti and subsequently patterned in several regions. In some embodiments, electrode 2 may be constructed from Pt/TiO$_2$ on SiO$_2$ or Pt/Ti or Au/Cr on a metal substrate or non-piezoelectric layer. One or both of electrodes 2 may also be patterned.

Electrodes 2 may be a thin layer of conductive material with a thickness of less than about 6000 nm, or less than about 300 nm, or less than about 200 nm, or less than about 100 nm, or less than about 90 nm, or less than about 80 nm.

Figure 1B:
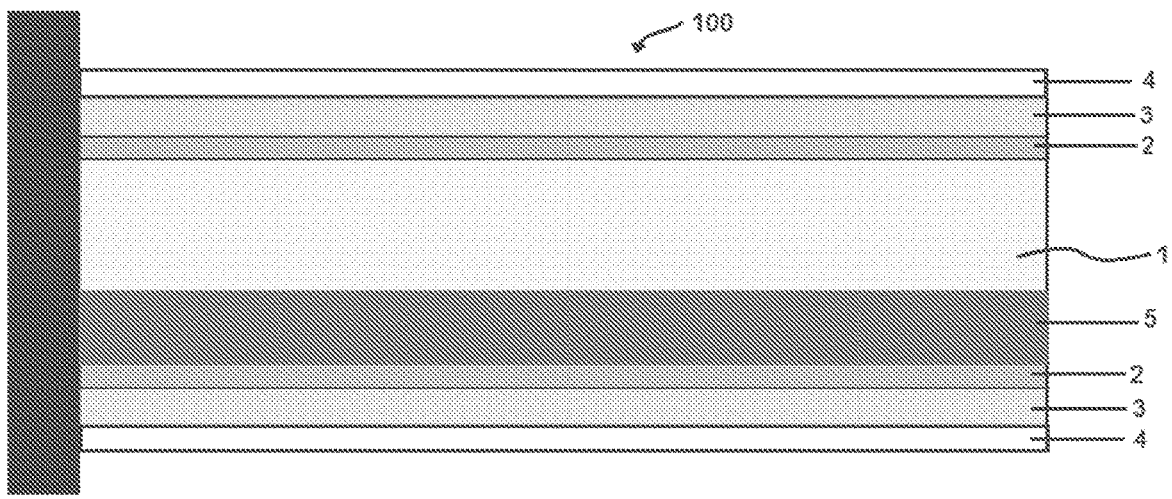
FIG. 1B shows a PEPS with a non-piezoelectric layer.

In some embodiments, a non-piezoelectric layer 5 is included in the PEPS 100 as shown in FIG. 1B. Non-piezoelectric layer 5 may be bonded to piezoelectric layer 1. Non-piezoelectric layer 5 may be made from any compatible material, including ceramic, polymeric, plastic, and/or metallic materials or any combination thereof. Non-piezoelectric layer 5 may be made from silicon dioxide (SiO$_2$), silicon nitride (Si$_3$N$_4$), a metal such as Cu, Sn, Ni, Ti, and stainless steel, or any combination thereof. Non-piezoelectric layer 5 may also have any structural configuration or dimension. Non-piezoelectric layer 5 may be rectangular, triangular, circular, elliptical, or have any other geometric shape. Non-piezoelectric layer 5 may have a length of from about 1 µm to about 5 mm, or from about 5 µm to about 5 mm, a width of from about 1 µm to about 5 mm, or from about 5 µm to about 5 mm, and a thickness of from about 0.05 µm to about 100 µm, or from about 0.1 µm to about 80 µm, or from about 1 µm to about 60 µm.

PEPS 100 may have a wide variety of structural configurations. Piezoelectric layer 1 may be bonded to a non-piezoelectric layer 5 that is shorter, longer or equal in length, or width.

Insulation layer 3 of the PEPS 100 may be made from mercaptopropyltrimethoxysilane (MPS) or other suitable insulating materials. The insulation layer 3 can electrically insulate the PEPS 100 when the sensor is used for detection in a salty biological fluid such as a serum or culture medium. In some embodiments, electrodes 2 may be patterned slightly smaller than piezoelectric layer 1 to ensure complete insulation of the edges and corners of electrodes 2.

In one embodiment, insulating layer 3 may comprise a 1.5 µm thick parylene (poly-para-xylylene) coating deposited on a conductive element 2 by chemical vapor deposition. When placed in static and 1 ml/min flow rate of PBS solution, a parylene insulating layer 3 essentially prevents background resonance frequency shifts greater than 30 Hz and 60 Hz, respectively, over a period of 30 minutes. As a result, insulating layer 3 can enable complete submersion of the sensor for in situ or in-liquid detection. Alternatively, a sensor may be insulated using self-assembled monolayers with hydrophobic properties, preferably methyltrimethoxysilane (MTMS) or a combination of MTMS with parylene coatings of varying thicknesses, may also be used.

Other insulation materials may include Al$_2$O$_3$, SiO$_2$ and any functional hydrophobic silane, having a hydrophobic group selected from the group consisting of alkyl, phenyl, alkyl halide, alkene, alkyne, and sulfhydryl. In an exemplary embodiment, the insulation material is mercaptopropylsilane (MPTS), which can also function to immobilize a receptor on the cantilever.

For detection of microbes, it is desirable to have a binding/receptor layer on an outer surface of the PEPS 100 that does not inhibit the microbes. For this purpose, an outer coating 4 of a material with suitably-arranged positive charges, suitably-mixed positive charges and negative charges, or microbe specific antibodies can be applied to the PEPS 100. One suitable material with mixed positive and negative charges for use as outer coating 4 is (3-aminopropyl) trimethoxysilane (APS) where the amine group provides the positive charge and the hydrosol of the silanol produced by hydrolysis of the silane group provides the negative charge. Examples of possible positively charged materials include poly-L lysine and polyethyleneimine (PEI) that may be coated and suitably arranged on the outer surface of the PEPS 100 to form the outer binding/receptor coating. A coating of antibodies specific to the microbe may be another embodiment of the outer binding/receptor coating.

Further details of the PEPS may be found, for example, in WO 2015/100170, the disclosure of which is hereby incorporated by reference in its entirety.

In general, the frequency of a resonance peak such as a length-extension-mode (LEM) resonance peak or a width-extension-mode (WEM) resonance peak of sensor such as a PEPS can change as a result of binding of a target species to the sensor. By monitoring resonance frequency shifts which result from binding of the target species, the system is capable of rapid, label-free, quantitative detection of various species using simple all-electrical measurements.

Since MPS is negatively charged, it is difficult to attract negatively charged microbes such as negatively charged bacteria to an MPS receptor. In such case, a layer of (3-Aminopropyl) trimethoxysilane (APS) can be coated onto the MPS insulation layer 3 to create a mixed-charge outer coating 4 to the sensor surface. In such an embodiment, the negative electric charge of the microbe facilitates bonding of the microbe to the positively charged amine group on the sensor surface. Alternatively, the outer coating layer can comprise an antibody specific to the microbe, suitably-arranged, positively-charged molecules such as poly-L lysine, PEI, or other materials suitable for binding the live microbes.

According to a preferred embodiment, bonding microbes to a piezoelectric sensor, such as a PEPS, requires several steps. First, after optional growth in vitro within a broth or agar plate or in vivo, the microbes to be tested should be isolated, such as with a centrifuge or other separation method, and the microbes may be suspended in deionized water, phosphate buffered saline (PBS) solution, growth broth, or any other suitable medium. The PEPS should subsequently be submerged in the microbe suspension, such as for 1-10 minutes, or else a small quantity (5 μl to 30 μl) of the microbe suspension should be placed on the PEPS. During this stage, the microbe (e.g. bacteria, parasites, or fungi) will be bound to the PEPS device. Subsequently, the PEPS device may be washed, preferably multiple times, with additional deionized water, PBS, or any buffer solution with a pH around 7, while the microbes remain bonded to the PEPS device.

As used in this invention, a piezoelectric sensor may be chemically inert, thermally stable and preferably miniaturized and properly fabricated to enhance sensitivity. In an exemplary embodiment, the piezoelectric sensor has a high detection sensitivity of about $1\times10^{-11}$ g/Hz or better, more preferably $1\times10^{-16}$ g/Hz or better and most preferably $1\times10^{-19}$ g/Hz or better. Preferably, the piezoelectric sensor has a detection sensitivity of about $1\times10^{-23}$ g/Hz or better.

In the operation of one embodiment, an alternating voltage may be applied to conductive element 2 to drive piezoelectric layer 1 of a self-actuating sensor and a conductive element 2 may be used to detect a shift in the mechanical resonance frequency of the sensor due to the binding of the microbes. During this process, a positive or negative change is introduced in the Young's modulus of the piezoelectric layer. In one exemplary embodiment, the change in the Young's modulus may be up to about 70%. The change in the Young's modulus of the piezoelectric layer is preferably greater than about 0.001%. Most preferably, the change in the Young's modulus may be about 0.001% to about 70%. One of the factors that induces a change in the Young's modulus is non-180° polarization domain switching. By inducing and/or enhancing non-180° polarization domain switching, it may be possible to further increase the detection sensitivity of the PEPS.

In an exemplary embodiment, the piezoelectric sensor may be operated in width extension mode, which is a type of linear extensional resonance mode, but it may also be operated in other resonance modes such as a length extension mode, a thickness extension mode, a flexural mode, a width shear mode, a length shear mode, a thickness shear mode or any other suitable resonance mode which is known to the art. Width mode enables more sensitive detection with high peak frequency intensities and minimized damping effects. In an exemplary embodiment, the piezoelectric sensor may be used at resonance frequencies within the range of about 1 kHz to about 10 GHz.

The systems described herein may be used in any of the AST methods of the present invention.'

In another aspect the system and method may employ software that executes algorithms to determine and report the MIC and an antimicrobial interpretive category, e.g. sensitive (S), intermediate (I) or resistant (R), based on guidelines from, for example, the United States Food and Drug Administration (FDA), the Clinical Laboratories Standard Institute (CLSI), the European Committee on Antimicrobial Susceptibility Testing (EUCAST), or any other organization. Suitable software will determine the MIC based on analysis of the top of the resonance peak as described above or analysis of the standard deviation.

One embodiment of an effective antimicrobial susceptibility test (AST) will employ an array of piezoelectric sensors which measure the effectiveness of various antibiotics and concentrations thereof. As they are simultaneously tested or tested in a series, each piezoelectric sensor within the array will demonstrate the effectiveness (e.g. antimicrobial activity) of the tested antimicrobial solution on the target microbes. While the number and arrangement of piezoelectric sensors within each array is largely immaterial to the invention, standard, rectangular 96-well plates may be used in one embodiment of the invention. In one embodiment, several sensors are coated with the same live microorganism and a number of different materials are tested, one or more with each sensor. In this manner, a plurality of different antibiotics or other antimicrobials can be screened simultaneously and/or a plurality different concentrations of antibiotics/antimicrobials can be tested simultaneously using, for example, an array of serial dilutions of the antibiotic.

Figure 2:
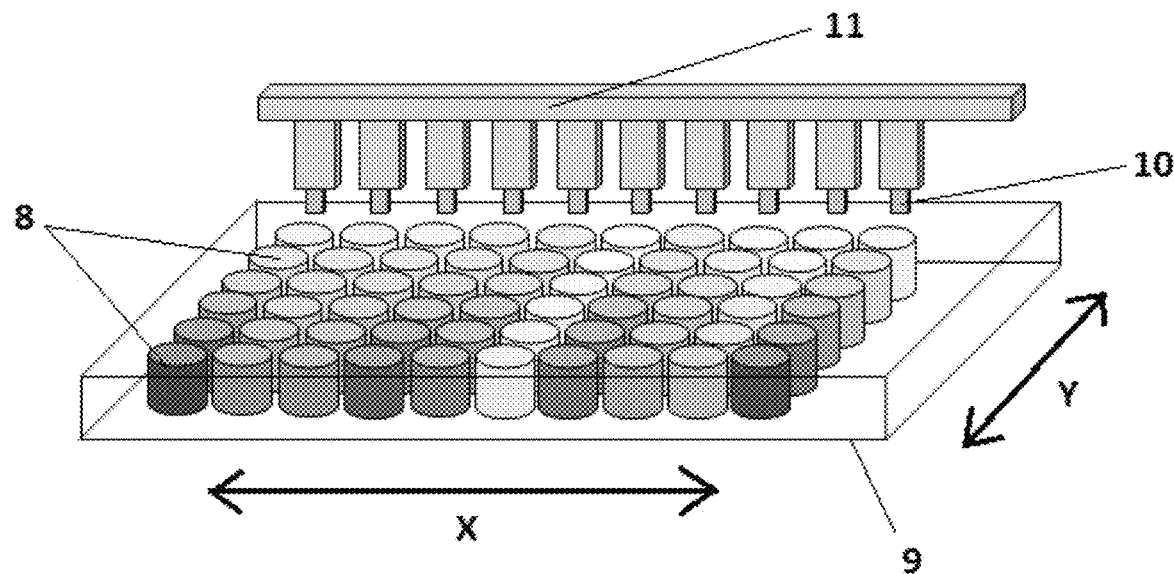
FIG. 2 shows how a 10 by 6 array of wells 8 within a tray 9 may be used as an AST test.

FIG. 2 shows how a 10 by 6 array of wells 8 within a tray 9 may be used as an AST test. Each well 8 in the X dimension (rows) contains a separate type of antimicrobial substance. Each well 8 in the Y dimension (columns) varies by the concentration of the antimicrobial substance within it. A single type of antimicrobial substance does not need to be used for the entirety of a row, but rather a row may be split between multiple antimicrobial substances. Similarly, a single antimicrobial substance may be tested with multiple rows. Likewise, the concentrations of the various antimicrobial substances across a given column need not be the same, but may vary according to the range of concentrations of the antimicrobial substances to be tested. Different types of antimicrobial substances at different concentrations may be combined within a well 8, for example for antimicrobial synergy testing.

The types of antimicrobial substances which can be tested by the present invention extend to any microbial substance known to the art, but for example may include amoxicillin, ampicillin, cefotetan, cefoxitin, chloramphenicol, clindamycin, imipenem, meropenem, metronidazole, mezlocillin, fluconazole, voriconazole, caspofungin, and amphotericin B. Concentrations of each substance tested may include a broad range of concentrations which can determine the MIC of each substance. For example, because AMP has a MIC with E. coli of 8 μg/ml, concentrations of AMP in an array of piezoelectric sensors with a target might include 0 μg/ml, 1 μg/ml, 2 μg/ml, 4 μg/ml, 8 μg/ml, and 16 μg/ml. In contrast, a limited range of antimicrobial concentrations (e.g. breakpoint concentrations) can be used to determine the MIC of each antimicrobial substance especially if the MIC for the microbe has been previously determined and is known. In general, sequential increases of the concentration of the antimicrobial substances may be useful to effectively and efficiently determine the MIC of an antimicrobial substance in relation to a target microbe.

Figure 3A:
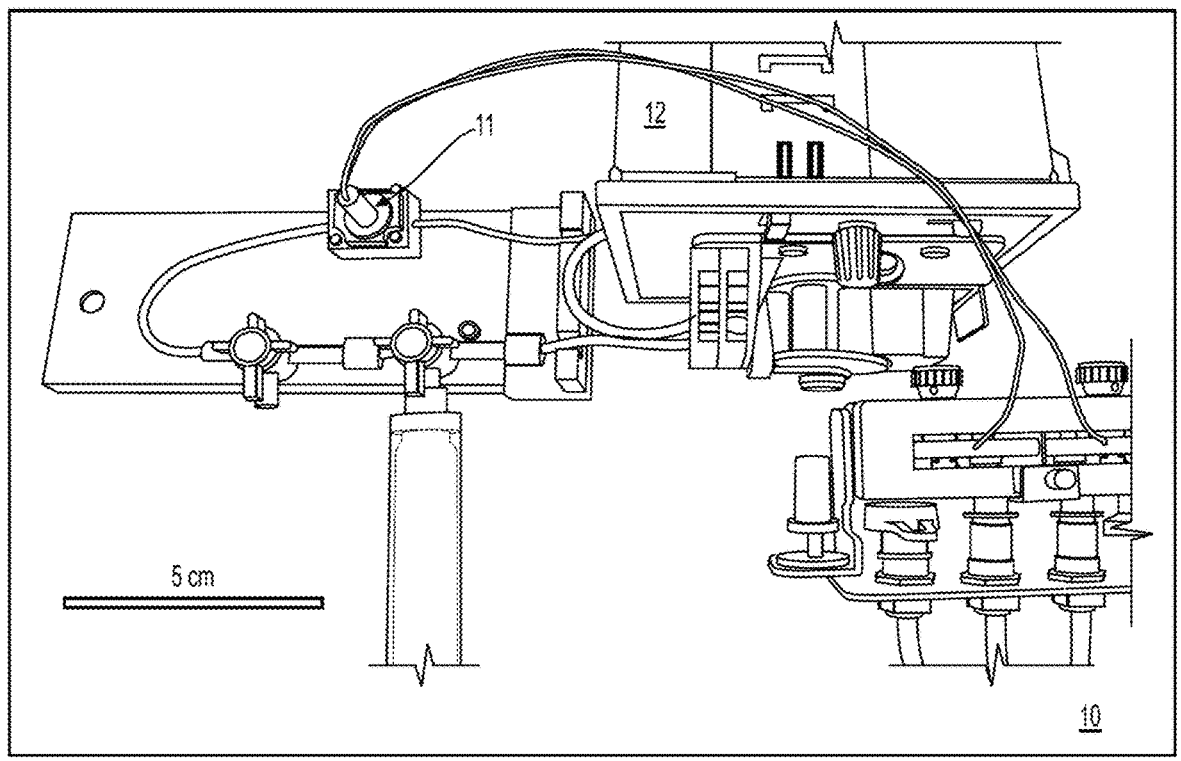
FIGS. 3(a)-3(b) show an exemplary connection of a computing device to the piezoelectric sensor used in the invention.
Figure 3B:
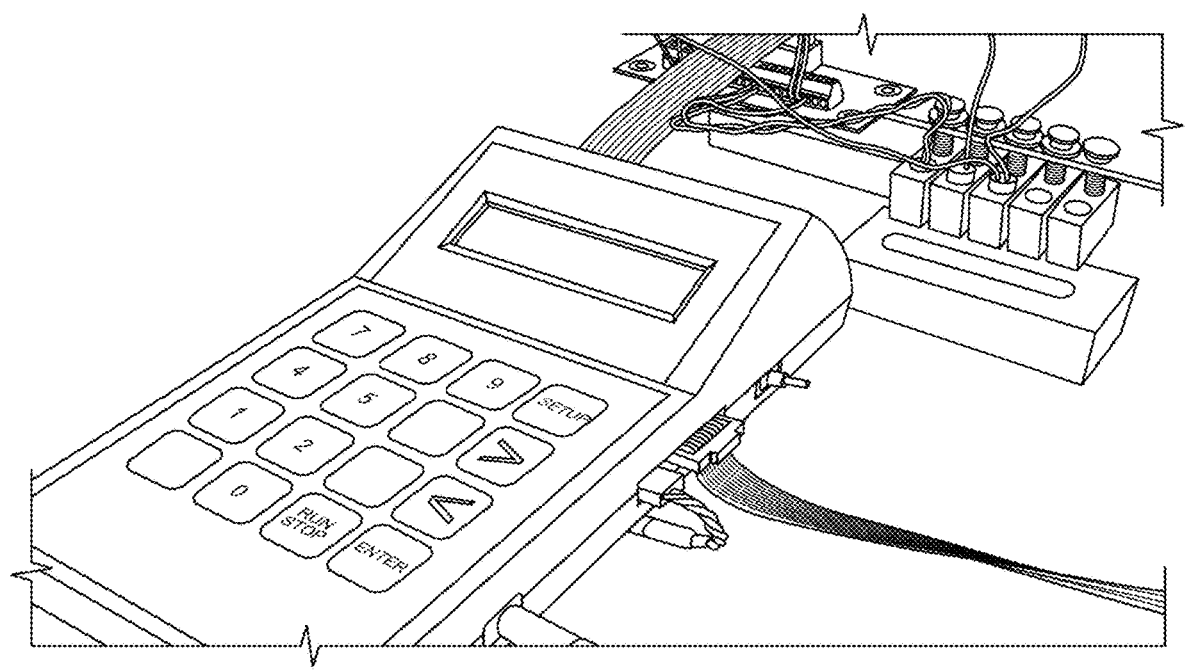

Piezoelectric sensors 10 to which the target microbes have been bound are submerged within each well 8. For accuracy in testing, more than one piezoelectric sensor may optionally be submerged within each well. The stresses produced by the live microbes may then be measured according to the disclosed methods, and the effectiveness of each concentration of each antimicrobial substance or antimicrobial combination may be determined. Apparatus 11 holds the piezoelectric sensors 10 to submerge them within the wells 8, and also comprises the electrical connections to the piezoelectric sensors 10 which enable the resonances of the piezoelectric sensors to be determined, measured, and recorded by a computing device 12. The connection of the computing device 12 to the piezoelectric sensors is shown by FIGS. 3a and 3b. Apparatus 11 can be of any configuration, such as holding a single piezoelectric sensor 10, an entire row of sensors 10 (as shown), an entire column of sensors 10, or a set of sensors which corresponds to the entire array of wells.

An alternative embodiment would not require wells, but rather the AST could be performed as different types and concentrations of antimicrobial substances are dropped, sprayed, or deposited on an array or sequence of piezoelectric sensors. The stresses produced by the live microbes on the piezoelectric sensors in such an embodiment could be measured in the same way and would also determine the effectiveness of each concentration of each antimicrobial substance.

EXAMPLES

Commercially available 127 μm thick PZT sheets (PSI-5H4E, Piezo Systems, INC., MA) were cut into 2.5 mm×1 mm squares using wire saw. They were soaked in acetone for 10 min to remove the wax and grease on the surface. Then both surfaces were connected with gold wires using conductive epoxy. The strip was fixed on a glass slide using non-conductive epoxy. The gold wires were connected to regular wires using the same conductive epoxy and they were wrapped in non-conductive epoxy for protection.

(3-Mercaptopropyl) trimethoxysilane (MPS) was used for electric insulation. Since MPS is negatively charged, it is difficult to attract the negatively charged bacteria. Therefore, a layer of (3-Aminopropyl) trimethoxysilane (APS) was coated onto the device after the MPS insulation to introduce positive charge to the sensor surface.

One protocol for MPS insulation was as follows:
1. Soak the sensor fixed on a glass slide substrate in Acetone in glass beaker for 1 min to remove the grease on the sensor surface
2. Soak the sensor in 5 ml of 100-fold diluted piranha solution (3 parts sulfuric acid and one part 30% hydrogen peroxide solution) in 50 ml centrifuge tube for 1 min at room temperature.
3. Rinse it by 5 ml of DI water in 50 ml centrifuge tube for 30 sec and then by 10 ml of ethanol in 50 ml centrifuge tube for 1 min.
4. After rinsing the sensor in ethanol, keep it at room temperature to dry for 5 min.
5. Soak the sensor in 10 ml of 0.1 mM MPS solution with 1% DI water in ethanol at pH=7.0 in a 50 ml centrifuge tube for 30 min at room temperature followed by repeating step 3.
6. Soak the sensor in 10 ml of 0.1% MPS solution with 0.5% DI water in ethanol at pH=8.0 in the 50 ml centrifuge tube for 12 h ten times (a total of 120 hours) at room temperature. To achieve pH=8.0,
   make KOH pellets powder by pounding
   exactly weigh 10 mg of KOH powder by using sensitive lab scales
   add 10 mg of KOH powder into 50 mL of 0.1% MPS solution with 0.5% DI water in ethanol
   shake it well and make sure all the powder dissolves in MPS solution.
7. To minimize the possible MPS cross-linking in the solution, after each 12 h MPS solution soaking, repeat step 3 and replenish the MPS solution with a fresh MPS solution of the same MPS concentration, water content, and pH.

One example protocol for APS coating was as follows:
1. After MPS insulation, rinse the sensor with 5 ml of DI water in a 50 ml centrifuge tube for 30 sec and then with 10 ml of ethanol in the 50 ml centrifuge tube for 1 min.
2. Keep the sensor at room temperature to dry for 5 min.
3. Soak the sensor in 10 ml of 0.1% APS solution with 0.5% deionized water in ethanol at pH=8.0 in a 50 ml centrifuge tube for 24 h at room temperature. To achieve pH=8.0,
   make KOH pellets powder by pounding,
   exactly weigh 10 mg of KOH powder by using sensitive lab scales,
   add 10 mg of KOH powder into 50 mL of 0.1% APS solution with 0.5% DI water in ethanol, and
   shake it well and make sure all the powder dissolves in APS solution.

Antimicrobial Susceptibility Testing Using PZT Sensors

After the PZT sensor was insulated with MPS and coated with APS, it was immersed in 5 ml of DI water to monitor the stability of width mode frequency peak for more than 30 min. If the peak was symmetric and stable, the sensor could be used for the antimicrobial testing.

E. coli suspension in broth was prepared. The concentration was about $10^9$ cells/mi. The following procedure was used to replace the broth with DI water, since the ions in the broth might affect the spectrum of the sensor. The suspension was centrifuged at 3000 rpm/min for 5 min and the supernatant was removed. 5 mL of DI water was then added to the tube and the E. coli was re-suspended in DI water.

For the first a few tests (Tests 1-3), a drop of E. coli suspension (20 μl) was put on the sensor surface. After 10 min, the sensor was washed with 400 ml of DI water in a glass beaker 3 times to remove the unbound bacteria. The sensor was then returned to 5 ml of DI water and its width mode peak was monitored. In Test 4, instead of putting a drop of suspension on the sensor, the sensor was soaked in the *E. coli* suspension for 10 min. The washing step for Test 4 was the same as mentioned above.

After the sensor with *E. coli* was monitored for 5-10 min, various amounts of ampicillin were added to the DI water every 5 min to determine whether the antibiotics would have an effect on the frequency peak. For Test 1, 1 mg/ml ampicillin solution was made. Different volumes of the ampicillin solution (5, 5, 10, 20, 40, and 120 μl) were added to the 5 ml of DI water to make the final concentrations of the ampicillin 1, 2, 4, 8, 16, and 32 μg/ml. In Tests 2-4 20 μl of ampicillin solutions of different concentrations (0.25, 0.25, 0.5, 1, 2, and 4 mg/ml) were added each time to make the final concentration of the ampicillin to 1, 2, 4, 8, 16, and 32 μg/ml.

Results

Figure 7:
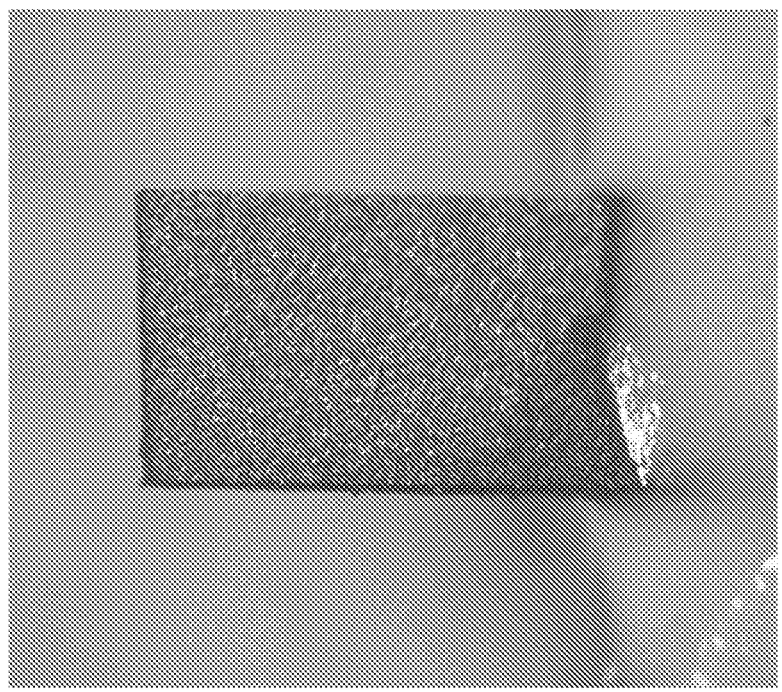
FIG. 7 is a photograph of the PZT PEPS used in Example 1.
Figure 8:
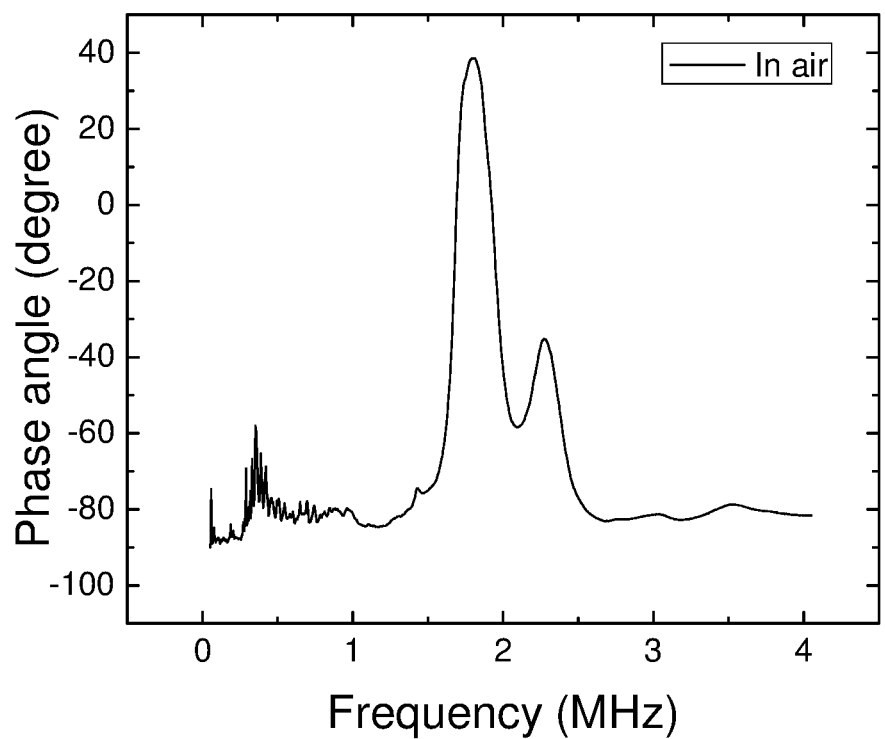
FIG. 8 shows the phase angle versus frequency spectrum of the sensor shown in FIG. 7 where the tallest peak at around 1.8 MHz is the first width extension mode (WEM), which was the resonance peak used in this example.
Figure 9:
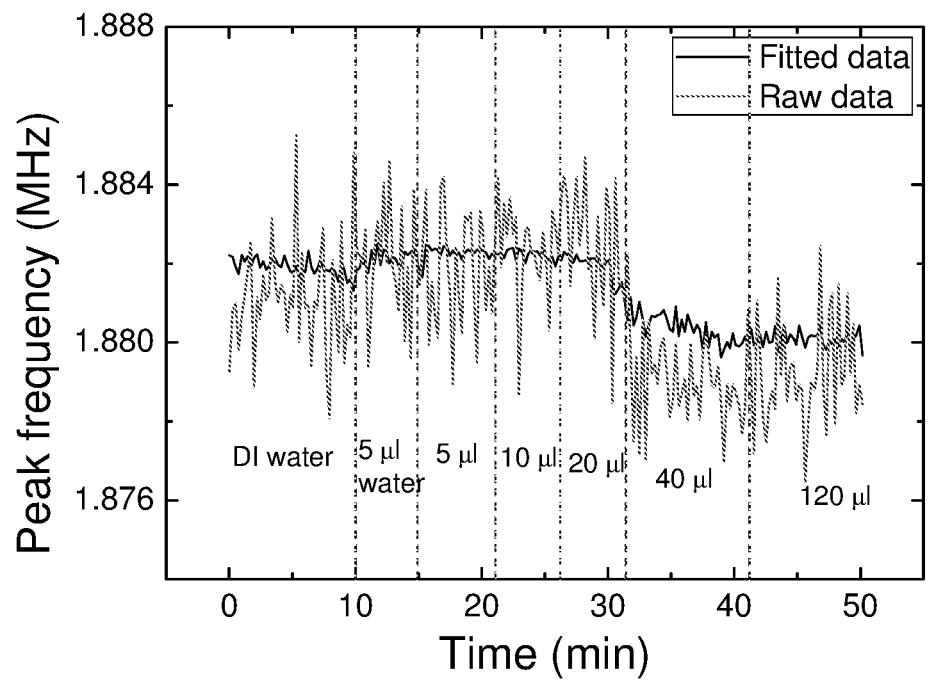
FIG. 9 shows the peak frequency of PZT PEPS monitored over time as different volumes of deionized water was added to the sensor.

A picture of the sensor used in these examples is shown in FIG. 7. The spectrum of the sensor is shown in FIG. 8. The length mode of the sensor consisted of multiple peaks and it was difficult to determine the peak position. The width mode of the sensor was very tall (30-40 degrees). So we used the width mode of the sensor for monitoring.

To test whether *E. coli* would be attracted to the APS coated surface, a regular glass slide was coated with APS using the protocol described above. The *E. coli* suspension (20 μl) was dropped on the glass slide. After 10 min, the glass slide was washed three times with 400 ml of DI water in a glass beaker. Under a microscope, it could be seen that there were lots of bacteria on the glass surface. Also, it was quite clear under the microscope that those bacteria were moving. For comparison, the same procedure was done with a regular glass slide without APS coating. It was obvious that there were no bacteria on the surface after washing.

Antimicrobial Susceptibility Testing Using PZT Sensors

In order to determine whether adding liquid would affect the peak frequency of the sensor, the PZT sensor without any bacteria was monitored in DI water. Instead of ampicillin solution, different amounts of DI water were added. As shown in FIG. 5, although the frequency changed after adding the water every time (especially after adding 40 μl of water), the standard deviation of peak frequency, both for the fitted data and raw data, did not significantly change as illustrated in Table 1. Therefore, in this case, the value of peak frequency cannot be directly used to determine whether adding antibiotics would affect the *E. coli*. Instead, it was necessary to use the standard deviation of the peak frequency to characterize it.

TABLE 1

The standard deviation (SD) of the fitted peak frequency and raw peak frequency in a blank control

| | | SD of fitted data (Hz) | SD of raw data (Hz) |
|---|---|---|---|
| DI water | | 212 | 1401 |
| Add DI water | 5 μl | 194 | 1336 |
| | 5 μl | 184 | 1418 |
| | 10 μl | 173 | 1341 |
| | 20 μl | 191 | 1168 |
| | 40 μl | 226 | 1068 |
| | 120 μl | 197 | 1316 |

Negative Control (No *E. coli*, with Ampicillin)

Figure 10:
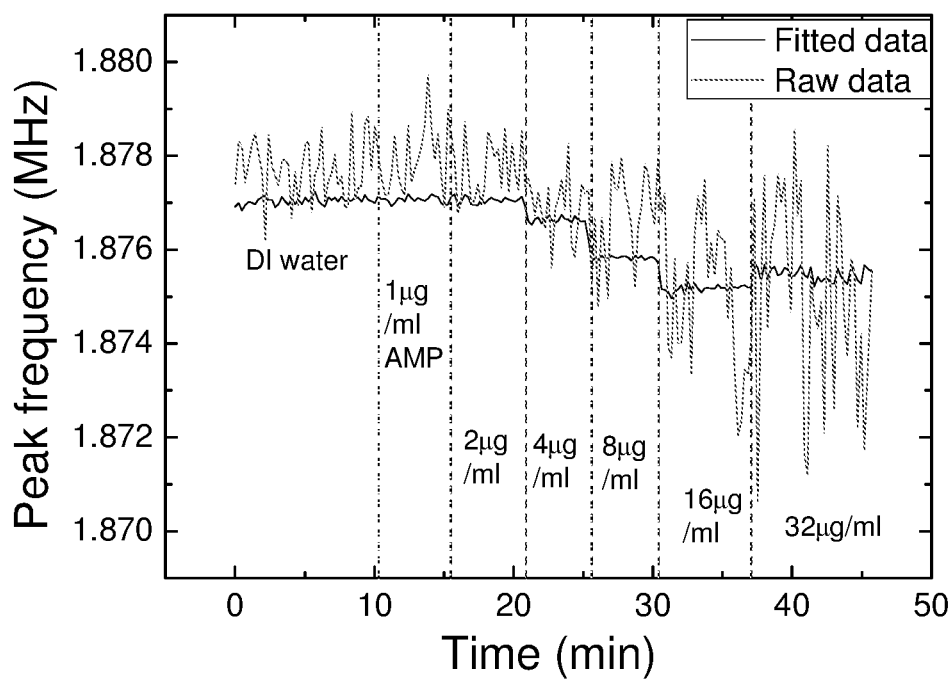
FIG. 10 shows the peak frequency of PZT sensor monitored over time as different volumes of ampicillin solutions (1 mg/ml, 5, 5, 10, 20, 40, and 120 μl) were added to make the final concentrations of ampicillin 1, 2, 4, 8, 16, and 32 μg/ml.

A negative control was carried out in which the PZT sensor without any bacteria on it was monitored in DI water. Different volumes of ampicillin solutions (1 mg/ml, 5, 5, 10, 20, 40, and 120 μl) were added to the DI water to make the final concentration of ampicillin to 1, 2, 4, 8, 16, and 32 μg/ml. The peak frequency of the sensor over time is shown in FIG. 10. It can be seen from the figure that after adding ampicillin solution, the peak frequency may change, which was consistent with the finding for the blank control. When the ampicillin concentration was low (i.e. 1 and 2 μg/ml), the standard deviation of the peak frequency was similar to that in DI water. When the ampicillin concentration continued to increase, the peak frequency was noisier and the standard deviation became getting larger and larger. This was true for both fitted peak frequency and the raw peak frequency as listed in Table 2.

TABLE 2

The standard deviation (SD) of the fitted and raw peak frequency in negative control

| | | SD of fitted data (Hz) | SD of raw data (Hz) |
|---|---|---|---|
| DI water | | 78 | 608 |
| Ampicillin | 1 μg/ml | 71 | 686 |
| | 2 μg/ml | 68 | 619 |
| | 4 μg/ml | 127 | 601 |
| | 8 μg/ml | 135 | 947 |
| | 16 μg/ml | 125 | 1584 |
| | 32 μg/ml | 145 | 2068 |

Antimicrobial Susceptibility Testing (Tests 1-3)

Figure 11A:
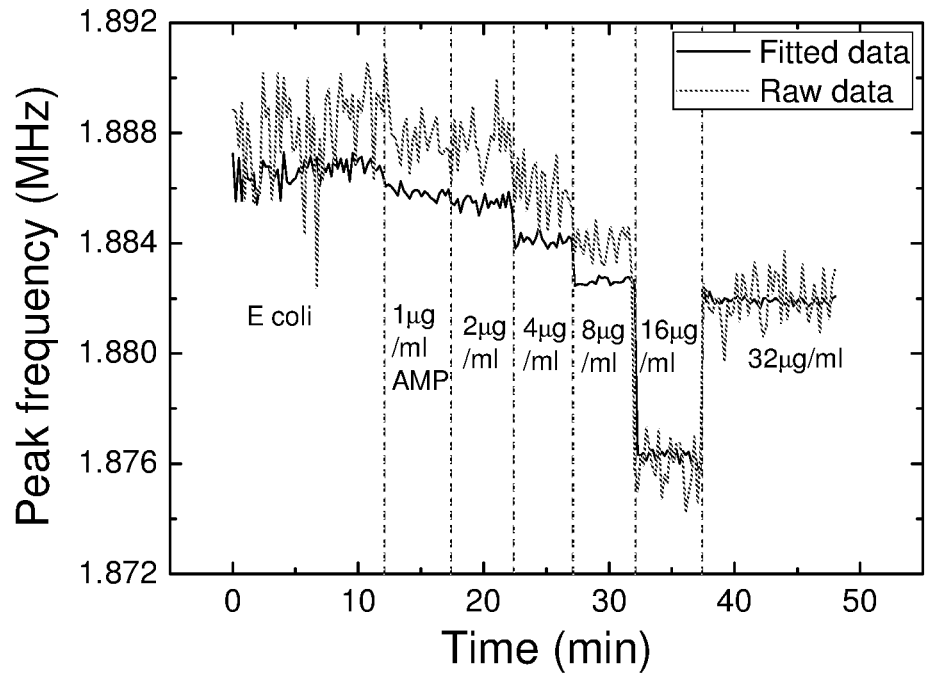
FIG. 11A shows the peak frequency in antimicrobial susceptibility Test 1 and FIG. 11B shows the standard deviation (SD) of fitted peak frequency and that of raw peak frequency in Test 1.
Figure 11B:
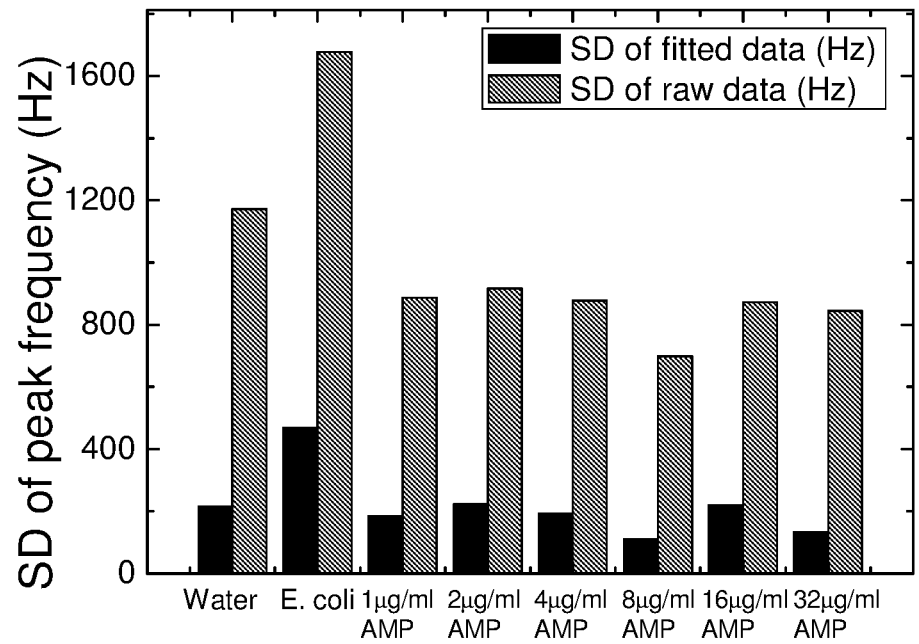
Figure 12A:
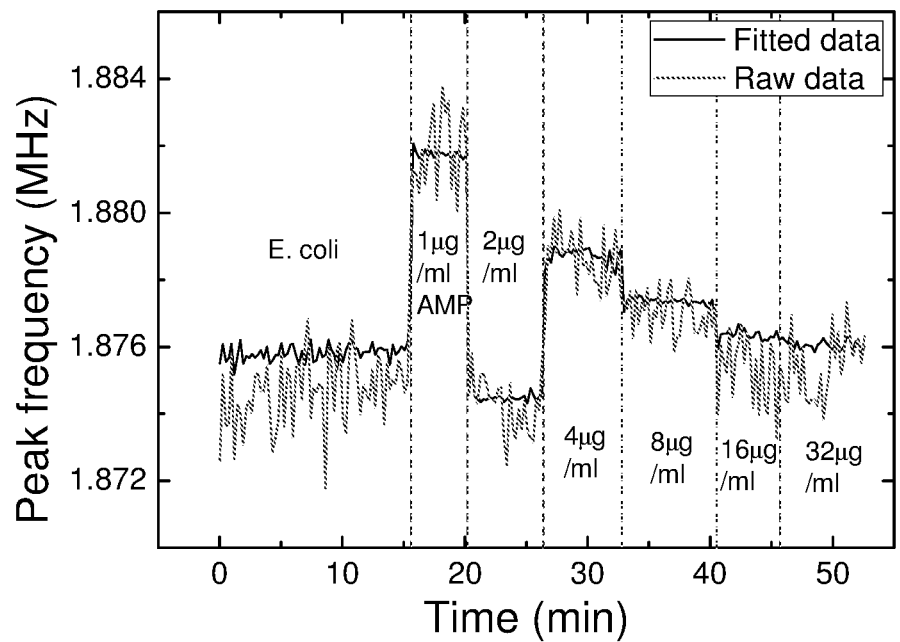
FIG. 12A shows the peak frequency in antimicrobial susceptibility Test 2 and FIG. 12B shows the standard deviation (SD) of fitted peak frequency and that of raw peak frequency in Test 2.
Figure 12B:
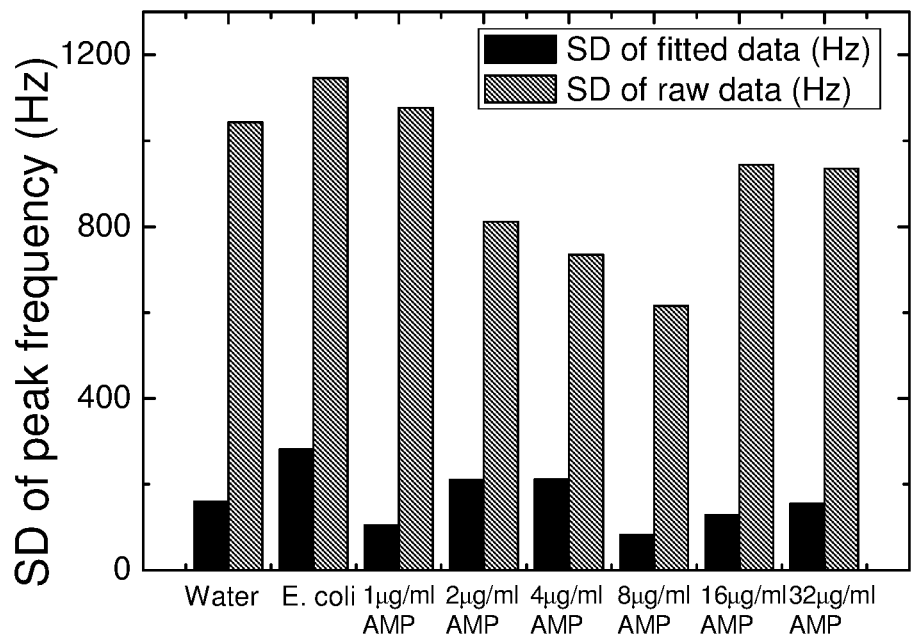
Figure 13A:
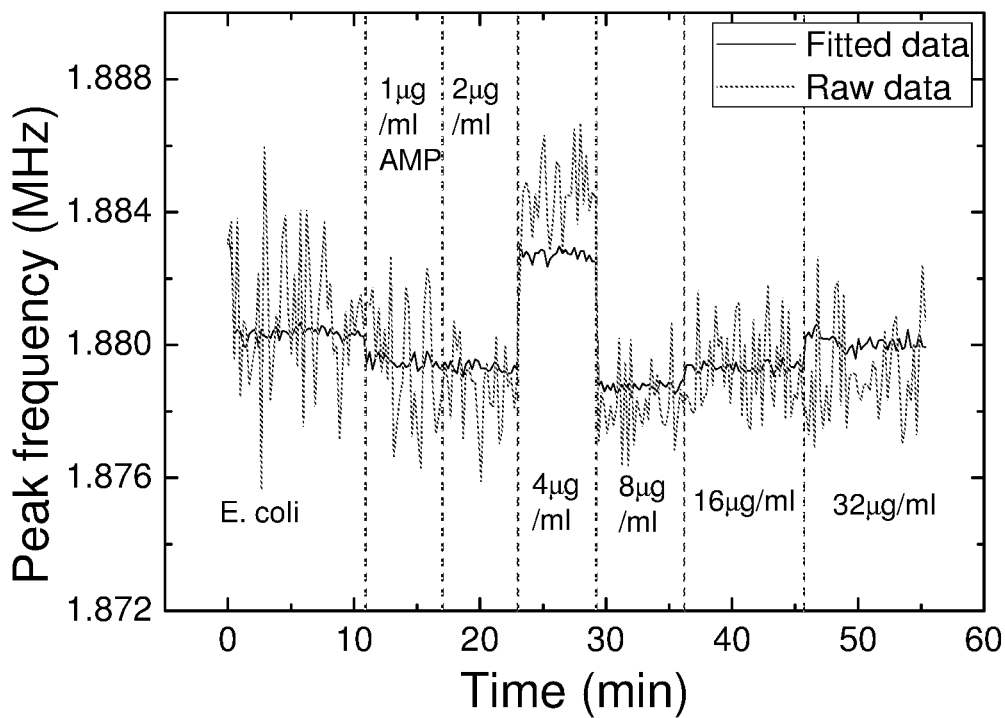
FIG. 13A shows the peak frequency in antimicrobial susceptibility Test 3 and FIG. 13B shows the standard deviation (SD) of fitted peak frequency and that of raw peak frequency in Test 3.
Figure 13B:
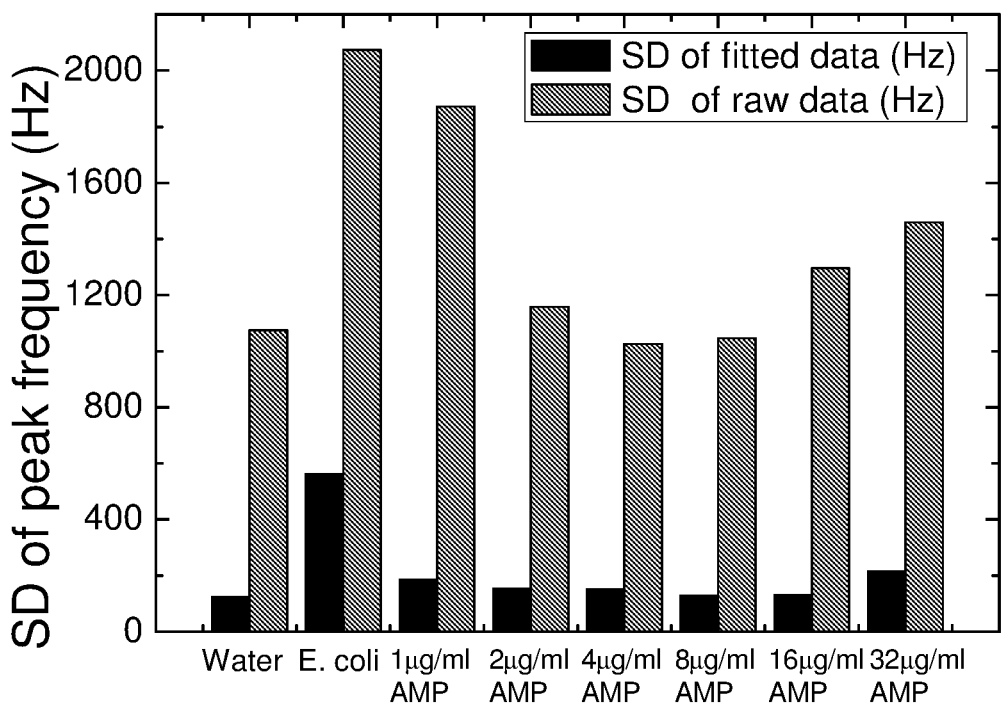

Three repeated Tests 1-3 were done for the antimicrobial susceptibility testing. The same sensor was used for all three tests. The peak frequency in Test 1 and its standard deviation (SD) change are shown in FIG. 11. Compared to the SD with *E. coli*, it is obvious that after adding the ampicillin, the SD decreased a lot. Adding more ampicillin lead to a further decrease in the SD of the peak frequency. The SD reached its minimal point when the concentration of the ampicillin was 8 μg/ml. After that, adding more ampicillin gave a slight increase in the SD. It was reasonable since we have found that larger concentrations of ampicillin would give more noise to the peak frequency. The results were similar in Tests 2 and 3.

Figure 14:
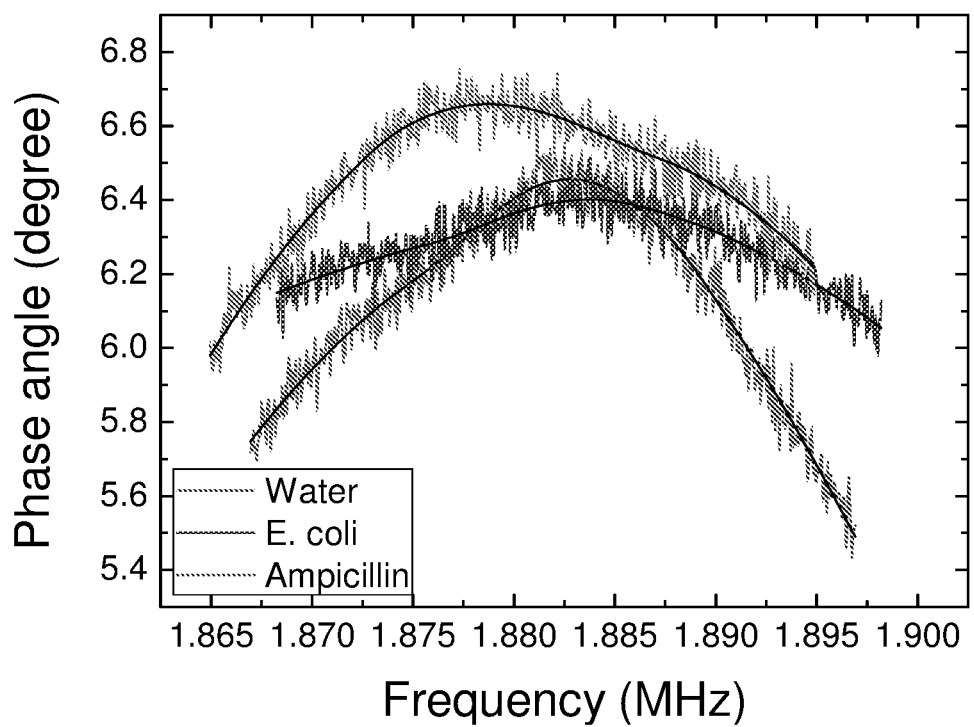
FIG. 14 shows the peak shapes of the PZT sensor in DI water (red), after adding *E. coli* (blue), and after adding ampicillin (8 μg/ml).

By looking at the peak shape of the PZT sensor at different conditions (in DI water, after adding *E. coli* on the sensor surface, and after adding ampicillin) as shown in FIG. 14, we found that with *E. coli* on the sensor, the peak shape became more flat. After adding ampicillin, the shape changed back to round. Therefore, by characterizing the roundness of the peak, it can be determined microbes such as bacteria located on the sensor surface were active or not.

Figure 15:
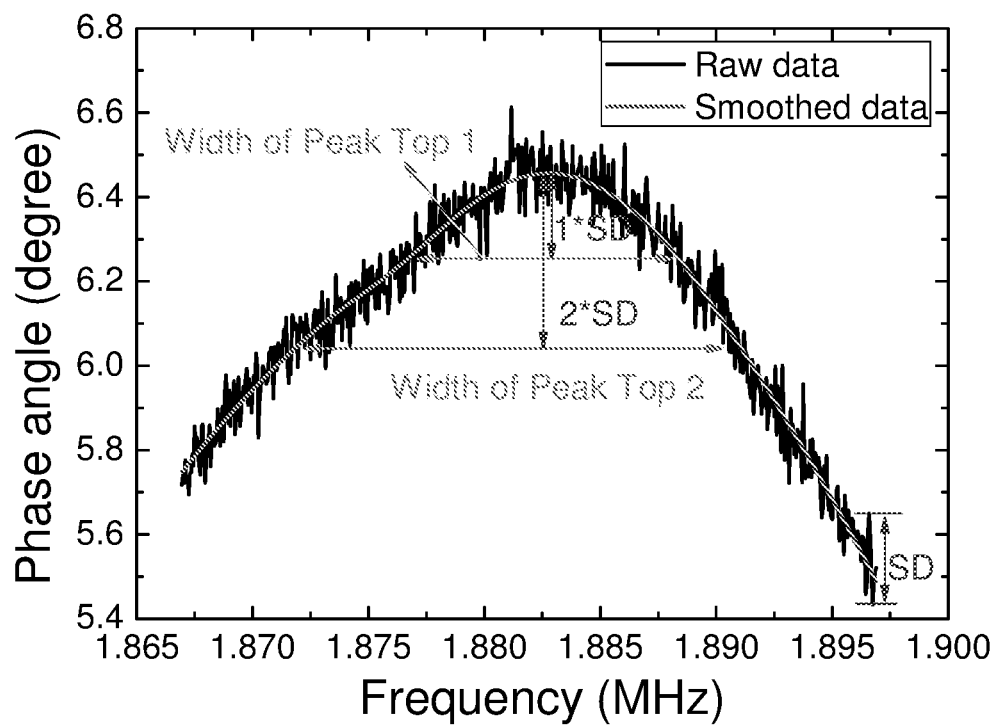
FIG. 15 is an illustration showing how to deduce the width of the top of the peak from the raw data to characterize the roundness of the peak.

To characterize the roundness of the peak shape, the raw data was smoothed first (as shown in FIG. 15. The amount of variation of the raw data from the smoothed data was calculated as the standard deviation (SD) of the raw data. The width of the top of the peak could be found when the phase angle was 1 times SD (or 2 times SD) smaller than the maximum phase angle in smoothed data. The more round the peak was, the smaller the width of the top of the peak would be. On the other hand, the more flat the peak was, the larger the width of the top of the top of the peak would be.

Figure 16A:
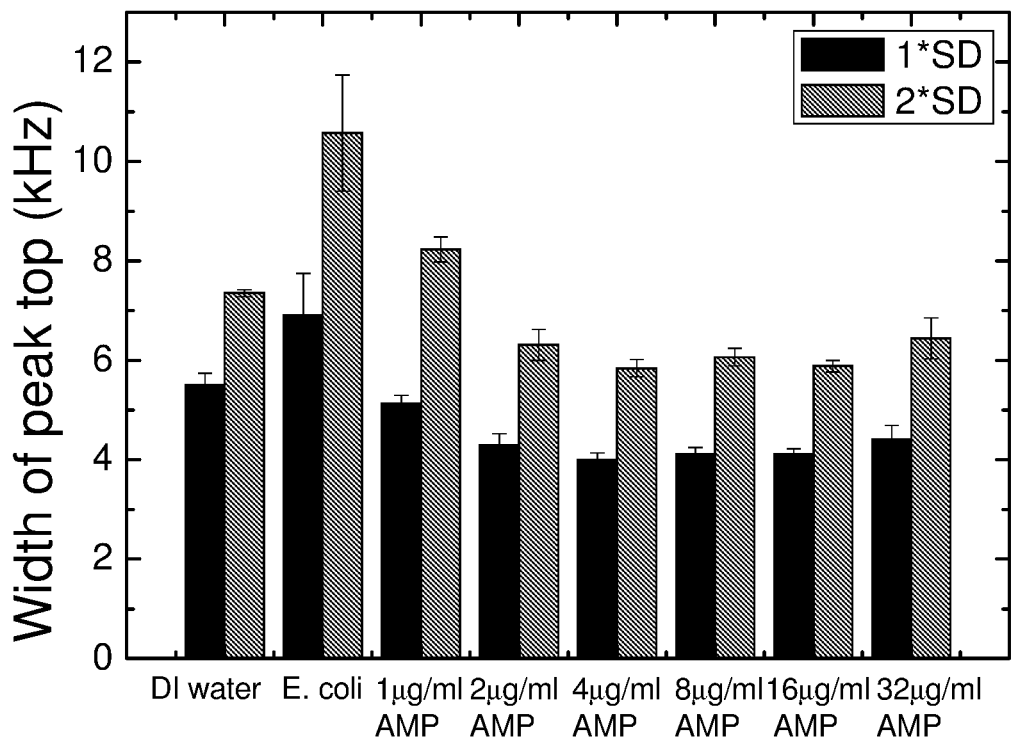
FIGS. 16A, 16B and 16C show the width of the top of the peak for the PZT sensor in Test 1, Test 2 and Test 3, respectively.
Figure 16B:
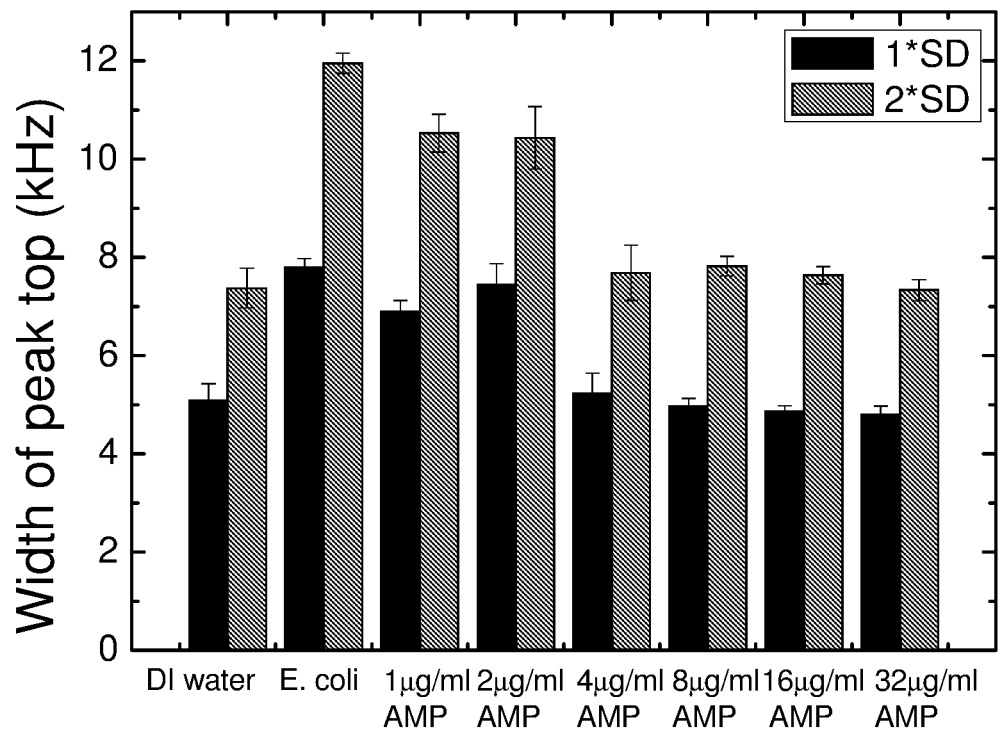
Figure 16C:
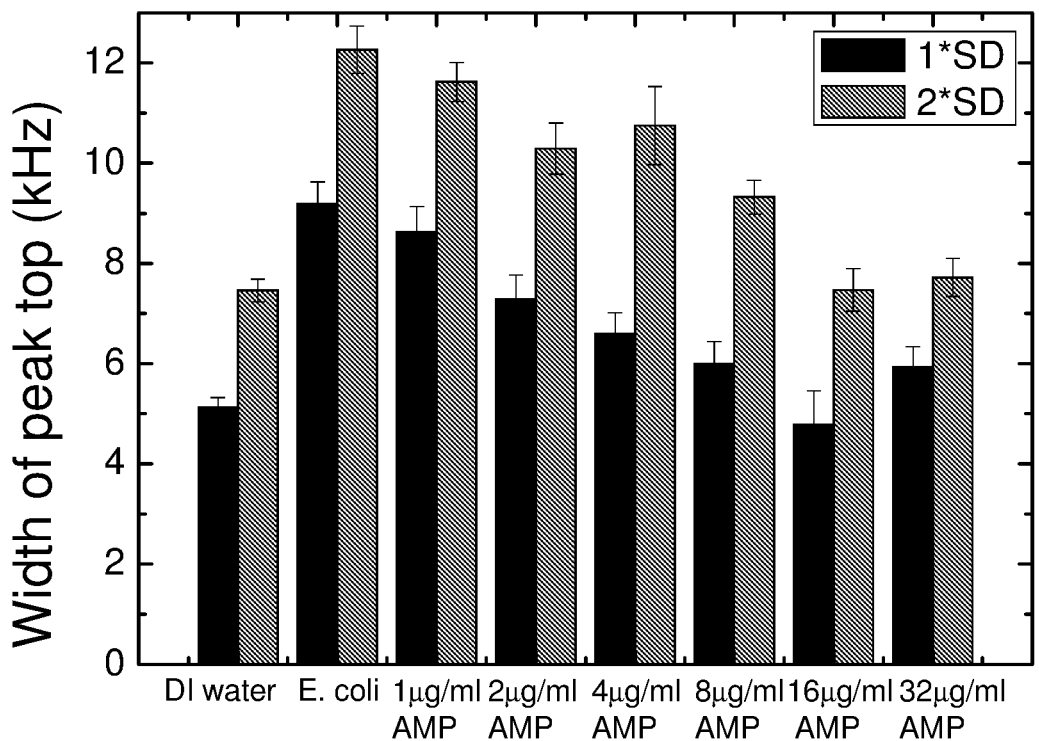

The widths of the top of the peak of the sensor in three AST tests are plotted in FIG. 16. With *E. coli* on the sensor, the width of the top of the peak increased significantly. After adding ampicillin, the width of the top of the peak started to decrease. When the ampicillin concentration was 4 or 8 μg/ml, the width of the top of the peak reached its minimum value. This was consistent with the fact that the MIC of ampicillin for that particular bacterial strain is 8 μg/ml. After that, adding more ampicillin would only cause a slightly change in the width of the top of the peak.

Negative Control 2 (No *E. coli*, with Ampicillin)

Figure 17A:
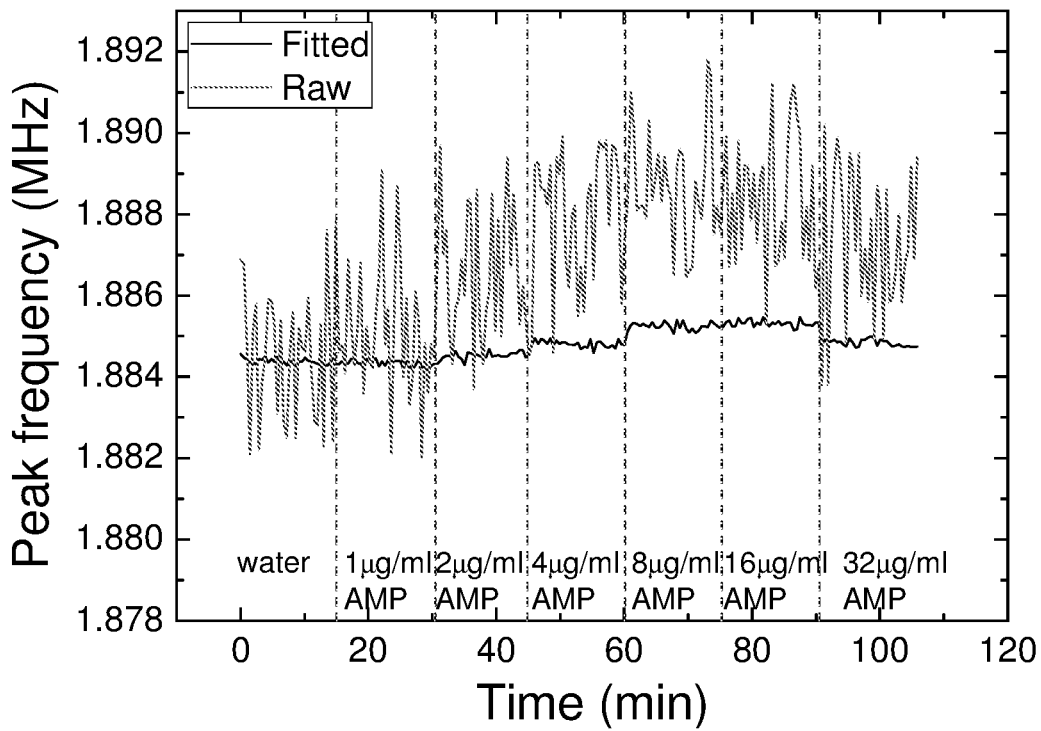
FIG. 17A shows the peak frequency of PZT sensor monitored over time and FIG. 17B shows the standard deviation of the peak frequency, when pH adjusted ampicillin solutions were added to it to make the final concentration of ampicillin 1, 2, 4, 8, 16, and 32 μg/ml.
Figure 17B:
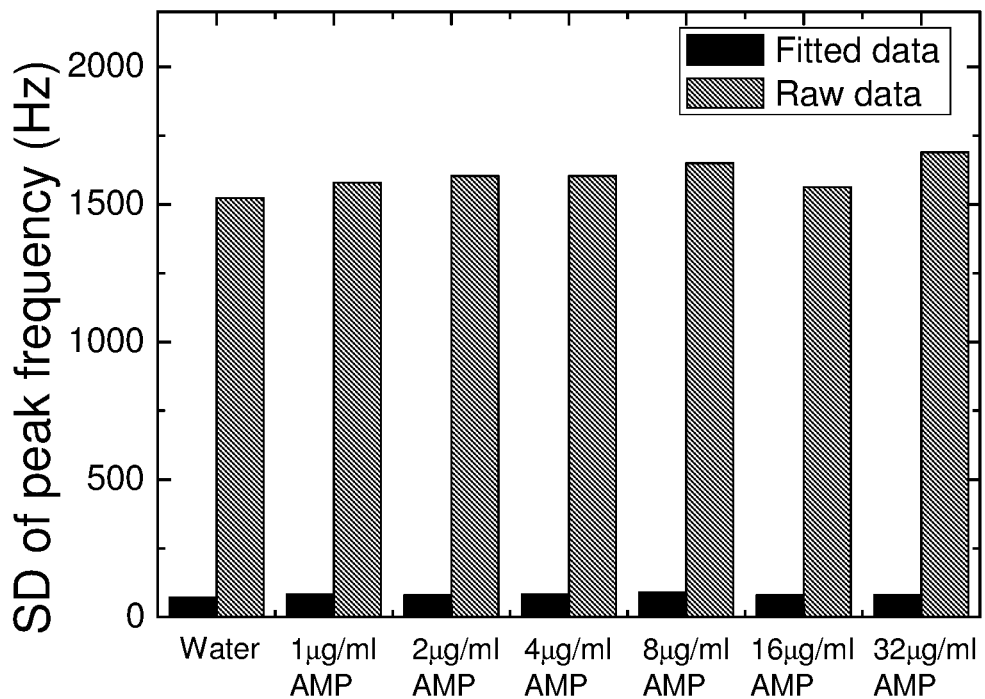

Larger concentrations of ampicillin added noise to the peak frequency of the sensor. Since ampicillin has both —NH$_2$ and —COOH groups, it was possible that the H$^+$ in the solution penetrated the insulation layer of the sensor and caused the instability. The pH value of the ampicillin solution (1 mg/ml) was measured using pH paper and it was found to be 3. To reduce the effect of H$^+$, the pH of the ampicillin solution was adjusted to 7 by adding KOH. The negative control was repeated. The PZT sensor without any bacteria on it was monitored in DI water. PH adjusted ampicillin solutions were added to the DI water to make the final concentration of ampicillin 1, 2, 4, 8, 16, and 32 µg/ml. The peak frequency versus time and the standard deviation of the frequency are shown in FIG. 17. It was clear that the standard deviation of the peak frequency was almost the same for different concentrations of ampicillin. This shows that adjustment of the pH of the ampicillin solution can reduce the noise to the sensor.

Antimicrobial Susceptibility Test (Test 4)

Figure 18A:
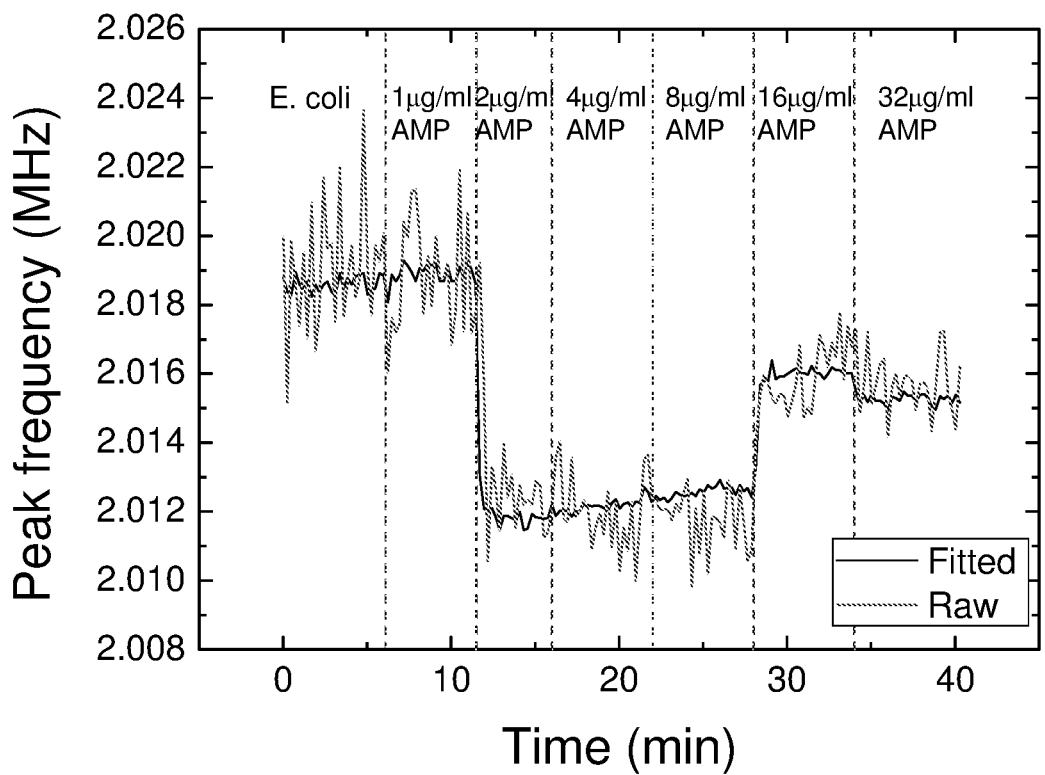
FIG. 18A shows the peak frequency in antimicrobial susceptibility test 4 and FIG. 18B shows the width of the top of the peak of the PZT sensor in Test 4.
Figure 18B:
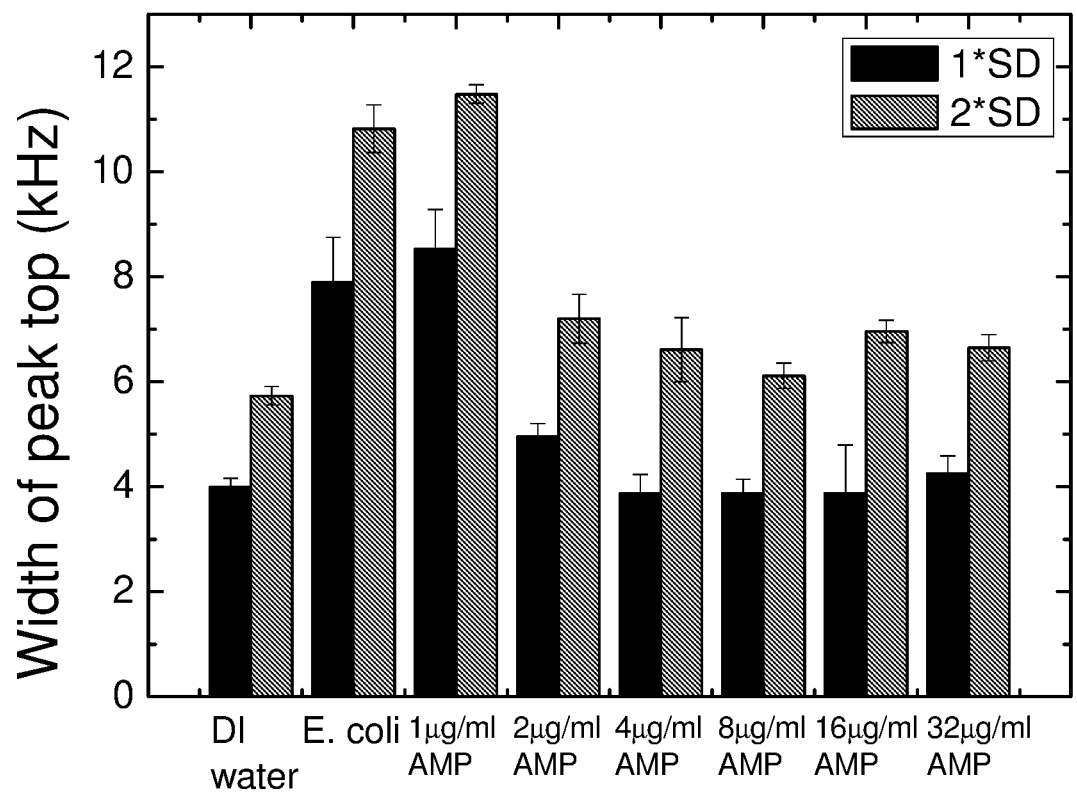

The antimicrobial susceptibility test was done using a different sensor. In this experiment, pH adjusted ampicillin was added to the sensor. The peak frequency of the sensor in the test was shown in FIG. 18A. After adding ampicillin, the peak frequency was less noisy. After more pH adjusted ampicillin was added, the noise did not increase. The width of the top of the peak is plotted in FIG. 18B. The width of the top of the peak increased as the *E. coli* was added the sensor surface and it decreased after ampicillin was added to the sensor. Adding more ampicillin did not further affect the width of the top of the peak.

What is claimed is:

1. A method of antimicrobial susceptibility testing including steps of:
    detecting a resonance peak of a sensor with live microbes on a surface portion of the sensor;
    contacting the live microbes on the surface portion of the sensor with a substance;
    detecting a resonance peak of said sensor after application of said substance;
    determining either a width of a top of said resonance peaks or a standard deviation of the frequency of said resonance peaks, and
    comparing the determined widths or standard deviations to determine antimicrobial susceptibility.

2. The method as claimed in claim 1 wherein the widths of the tops of the resonance peaks are determined from one of: (1) a phase angle versus frequency plot where the phase angle is the phase angle of the electrical impedance of the sensor, (2) a real part of a plot of an electrical impedance versus frequency of the sensor, (3) a plot of a magnitude of the electrical impedance versus frequency of the sensor, and (4) a phase angle versus frequency plot where the phase angle is the phase angle between an output voltage and an input voltage of the sensor.

3. The method as claimed in claim 2 wherein the widths of the tops of the resonance peaks are determined from the phase angle versus frequency plot where the phase angle is the phase angle of the electrical impedance of the sensor.

4. The method as claimed in claim 3, wherein the top of each of the resonance peaks is a portion of the resonance peak that is within a vertical distance of a highest point of the resonance peak that is larger than a standard deviation of the phase angles of the electrical impedance and less than about one thousand times the standard deviation of the phase angles of the electrical impedance.

5. The method as claimed in claim 3, wherein the top of each of the resonance peaks is a portion of the resonance peak that is within a distance from a highest point of the resonance peak larger than 0.01% of a total height of the resonance peak and a distance smaller than 10% of the total height of the resonance peak.

6. The method as claimed in claim 2 wherein the widths of the tops of the resonance peaks are determined from the real part of a plot of the electrical impedance versus frequency of the sensor.

7. The method as claimed in claim 6, wherein the top of each of the resonance peaks is a portion of the resonance peak that is within a vertical distance of a highest point of the resonance peak that is larger than a standard deviation of the real part of the electrical impedance and less than about one thousand times the standard deviation of the real part of the electrical impedance.

8. The method as claimed in claim 6, wherein the top of each of the resonance peaks is a portion of the resonance peak that is within a distance from a highest point of the resonance peak larger than 0.01% of a total height of the resonance peak and a distance smaller than 10% of the total height of the resonance peak.

9. The method as claimed in claim 2 wherein the widths of the tops of the resonance peaks are determined from the plot of the magnitude of the electrical impedance versus frequency of the sensor.

10. The method as claimed in claim 9, wherein the top of each of the resonance peaks is a portion of the resonance peak that is within a vertical distance of a highest point of the resonance peak that is larger than a standard deviation of the magnitude of the electrical impedance and less than about one thousand times the standard deviation of the magnitude of electrical impedance versus frequency.

11. The method as claimed in claim 9, wherein the top of each of the resonance peaks is a portion of the resonance peak that is within a distance from a highest point of the resonance peak larger than 0.01% of a total height of the resonance peak and a distance smaller than 10% of the total height of the resonance peak.

12. The method as claimed in claim 2 wherein the widths of the tops of the resonance peaks are determined from the phase angle versus frequency plot where the phase angle is the phase angle between the output voltage and the input voltage of the sensor.

13. The method as claimed in claim 12, wherein the top of each of the resonance peaks is a portion of the resonance peak that is within a vertical distance of a highest point of the resonance peak that is larger than a standard deviation of the phase angle between the output voltage and the input voltage and less than about one thousand times the standard deviation of the phase angle between the output voltage and the input voltage.

14. The method as claimed in claim 12, wherein the top of each of the resonance peaks is a portion of the resonance peak that is within a distance from a highest point of the resonance peak larger than 0.01% of a total height of the resonance peak and a distance smaller than 10% of the total height of the resonance peak.

15. The method of claim 1, wherein the method is performed using a plurality of sensors, with the live microbes on the surface portion of the sensor; different amounts of the substance are applied to said microbes on each said sensor; and both of said detecting steps are performed with each said sensor and said determining and comparing steps are performed using output from each said sensor.

16. The method of claim 1, wherein the method is performed using a plurality of sensors, the live microbes on the surface portion of the sensor; different substances are applied to said microbes on each said sensor; and both of said detecting steps are performed with each said sensor and said determining and comparing steps are performed using output from each said sensor.

17. The method of claim 1, wherein the method is performed using a plurality of sensors, the live microbes on the surface portion of the sensor; different types of substance are applied to said microbes on at least two said sensors and different amounts of at least one said substance are applied to at least two said sensors; and both of said detecting steps are performed with each said sensor and said determining and comparing steps are performed using output from each said sensor.

18. The method of claim 1, wherein in the detecting step, the sensor is operated in one of a flexural mode, a length extension mode, a width extension mode, a thickness extension mode, a length shear mode, a width shear mode, a thickness shear mode, or a combination of any of the above modes.

19. The method of claim 18, wherein in the detecting step, the sensor is operated in a width extension mode.

20. A system for rapid antimicrobial susceptibility testing comprising:
- a plurality of sensors having at least one outer surface portion,
- an apparatus for detecting a resonance of the plurality of sensors at a plurality of frequencies; and
- a processing system configured to:
    - determine a width of a top of first and second detected resonance peaks of at least one said sensor from one of: (1) a phase angle versus frequency plot where the phase angle is the phase angle of the electrical impedance of the sensor, (2) a real part of a plot of an electrical impedance versus frequency of the sensor, (3) a plot of a magnitude of electrical impedance versus frequency of the sensor, and (4) a phase angle versus frequency plot where the phase angle is the phase angle between an output voltage and an input voltage of the sensor, and
    - compare the determined widths or standard deviations to determine antimicrobial susceptibility, and
- wherein the top of a resonance peak is determined as claimed in any one of claims 4-5, 7-8, 10-11 and 13-14.

* * * * *